(12) United States Patent
Wittrup et al.

(10) Patent No.: US 8,906,356 B2
(45) Date of Patent: Dec. 9, 2014

(54) MUTANT INTERLEUKIN-2 (IL-2) POLYPEPTIDES

(75) Inventors: K. Dane Wittrup, Chestnut Hill, MA (US); David V. Liu, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 21 days.

(21) Appl. No.: 12/741,552

(22) PCT Filed: Nov. 5, 2008

(86) PCT No.: PCT/US2008/082528
§ 371 (c)(1),
(2), (4) Date: Dec. 13, 2010

(87) PCT Pub. No.: WO2009/061853
PCT Pub. Date: May 14, 2009

(65) Prior Publication Data
US 2011/0091412 A1 Apr. 21, 2011

Related U.S. Application Data

(60) Provisional application No. 60/985,532, filed on Nov. 5, 2007.

(51) Int. Cl.
*C07K 14/55* (2006.01)
*A61K 38/20* (2006.01)
(52) U.S. Cl.
CPC .................................... *C07K 14/55* (2013.01)
USPC ........................................ 424/85.2; 530/351
(58) Field of Classification Search
CPC ...................................................... C07K 14/55
USPC .................................................. 424/85.2, 351
See application file for complete search history.

(56) References Cited

U.S. PATENT DOCUMENTS

| | | | |
|---|---|---|---|
| 4,853,332 A | | 8/1989 | Mark et al. |
| 5,116,964 A | * | 5/1992 | Capon et al. ................. 536/23.5 |
| 6,451,308 B1 | | 9/2002 | Strom et al. |
| 6,617,135 B1 | | 9/2003 | Gillies et al. |
| 7,569,215 B2 | * | 8/2009 | Wittrup et al. ............... 424/85.2 |
| 7,951,360 B2 | * | 5/2011 | Wittrup et al. ............... 424/85.2 |

FOREIGN PATENT DOCUMENTS

WO 99/60128 A1 11/1999

OTHER PUBLICATIONS

Mikayama et al. Proc. Natl. Acad. Sci. USA (1993) vol. 90, pp. 10056-10060.*
Voet et al. Biochemistry John Wiley & Sons, Inc. (1990), pp. 126-128 and 228-234.*
Rao, Balaji M. et al., "Interleukin-2 mutants with enhanced alpha-receptor subunit binding affinity," Protein Engineering, vol. 16(12):1081-1087 (2003).
Raymond, Christopher K. et al., "General Method for Plasmid Construction Using Homologous Recombination," BioTechniques, vol. 26:134-141 (1999).
Saggio, Isabella et al., "CNTF variants with increased biological potency and receptor selectivity define a functional site of receptor interaction," The EMBO Journal, vol. 14(13):3045-3054 (1995).
Shanafelt, Armen B. et al., "A T-cell-selective interleukin 2 mutein exhibits potent antitumor activity and is well tolerated in vivo," Nature Biotechnology, vol. 18:1197-1202 (2000).
Smith, Kendall A., "Cell Growth Signal Transduction Is Quantala," Receptor Activation by Antigens, Cytokines, Hormones and Growth Factors, vol. 766:263-271 (1995).
Smith, Kendall A., "Lowest Dose Interleukin-2 Immunotherapy," Blood, vol. 81(6):1414-1423 (1993).
Smith, Kendall A., "The Interleukin 2 Receptor," Annu. Rev. Cell Biol., vol. 5:397-425 (1989).
Stauber, Deborah J. et al., "Crystal structure of the IL-2 signaling complex: Paradigm for a heterotrimeric cytokine receptor," PNAS, vol. 103(8):2788-2793 (2006).
Teshigawara, Keisuke et al., "Interleukin 2 High-Affinity Receptor Expression Requires Two Distinct Binding Proteins," J. Exp. Med., vol. 165:223-238 (1987).
Theze, Jacques et al., "Interleukin 2 and its receptors: recent advances and new immunological functions," Immunology Today, vol. 17:481-486 (1996).
Toniatti, Carlo et al., "Engineering human interleukin-6 to obtain variants with strongly enhanced bioactivity," The EMBO Journal, vol. 15(11):2726-2737 (1996).
Voet, Donald et al., Biochemistry, John Wiley & Sons, Inc., pp. 126-128, 228-234 (1990).
Voss, Stephan D. et al., "Characterization of the Interleukin 2 Receptors (IL-2R) Expressed on Human Natural Killer Cells Activated In Vivo by IL-2: Association of the p64 IL-2R gamma Chain with the IL-2R beta Chain in Functional Intermeidate-Affinity IL-2R," J. Exp. Med., vol. 176:531-541 (1992).
Waldmann, Thomas A. et al., "Contrasting Roles of IL-2 and IL-15 in the Life and Death of Lymphocytes: Implications of Immunotherapy," Immunity, vol. 14:105-110 (2001).
Wang, Xinquan et al., "Structure of the Quaternary Complex of Interleukin-2 with Its alpha, beta, and gammac Receptors," Science, vol. 310:1159-1163 (2005).
Wu, Zining et al., "Solution assembly of the pseudo-high affinity and intermediate affinity interleukin-2 receptor complexes," Protein Sciences, vol. 8:482-489 (1999).
Zaccolo, Manuela et al., "An Approach to Random Mutagenesis of DNA Using Mixtures of Triphosphate Derivatives of Nucleoside Analogues," J. Mol. Biol., vol. 255:589-603 (1996).

(Continued)

*Primary Examiner* — Prema Mertz
(74) *Attorney, Agent, or Firm* — Nelson Mullins Riley & Scarborough LLP; Amy E. Mandragouras, Esq.; Christopher L. Frank

(57) ABSTRACT

The present invention relates to mutant IL-2 polypeptides that act as receptor antagonists. The mutant IL-2 polypeptides bind CD 25 but do not activate the IL-2 receptor. Also provided are methods of using the mutant IL-2 polypeptides, for example, to treat a patient who has cancer or a viral infection. The mutant polypeptides can also be used in various delivery systems.

27 Claims, 9 Drawing Sheets

(56) References Cited

OTHER PUBLICATIONS

Zaccolo, Manuela et al., "The Effect of High-frequency Random Mutagenesis on in Vitro Protein Evolution: A Study on TEM-1 beta-Lactamase," J. Mol. Biol., vol. 285:775-783 (1999).
Arima, Nobuyoshi et al., "Pseudo-High Affinity Interleukin 2 (IL-2) Receptor Lacks the Third Component That Is Essential for Functional IL-2 Binding and Signaling," J. Exp. Med., vol. 176:1265-1272 (1992).
Atkins, Michael B. et al., "High-Dose Recombinant Interleukin 2 Therapy for Patients With Metastatic Melanoma: Analysis of 270 Patients Treated Between 1985 and 1993," Journal of Clinical Oncology, vol. 17(7):2105-2116 (1999).
Berndt, William G. et al., "Mutagenic Analysis of a Receptor Contact Site on Interleukin-2: Preparation of an IL-2 Analog with Increased Potency," Biochemistry, vol. 33:6571-6577 (1994).
Blanar, Michael A. et al., "Interaction Cloning: Identification of a Helix-Loop-Helix Zipper Protein That Interacts with c-Fos," Science, vol. 256:1014-1018 (1992).
Boder, Eric T. et al., "Yeast Surface Display for Directed Evolution of Protein Expression, Affinity, and Stability," Methods in Enzymology, vol. 328:430-444 (2000).
Boder, Eric T. et al., "Yeast surface display for screening combinatorial polypeptide libraries," Nature Biotechnology, vol. 15:553-557 (1997).
Buchli, Pamela J. et al., "The Functional Display of Interleukin-2 on Filamentous Phage," Archives of Biochemistry and Biophysics, vol. 339(1):79-84 (1997).
Buchli, Pamela J. et al., "Structural and Biologic Properties of a Human Aspartic Acid-126 Interleukin-2 Analog," Archives of Biochemistry and Biophysics, vol. 307(2):411-415 (1993).
Cassell, Delanie J. et al., "Therapeutic Enhancement of IL-2 Through Molecular Design," Current Pharmaceutical Design, vol. 8:2171-2183 (2002).
Collins, L. et al., "Identification of specific residues of human interleukin 2 that affect binding to the 70-kDa subunit (p70) of the interleukin 2 receptor," Proc. Natl. Acad. Sci. USA, vol. 85:7709-7713 (1988).
Dubois, Sigrid et al., "IL-15Ralpha Recycles and Presents IL-15 in trans to Neighboring Cells," Immunity, vol. 17:537-547 (2002).
Dudley, Mark E. et al., "Cancer Regression and Autoimmunity in Patients After Clonal Repopulation with Antitumor Lymphocytes," Science, vol. 298(5594):850-854 (2002).
Eckenberg, Ralph et al., "Analysis of Human IL-2/IL-2 Receptor beta Chain Interactions: Monoclonal Antibody H2-8 and New IL-2 Mutants Define the Critical Role of alpha Helix-A of IL-2," Cytokine, vol. 9(7):488-498 (1997).
Eicher, Donald M. et al., "IL-2Ralpha on One Cell Can Present IL-2 to IL-2R/gammac on Another Cell to Augment IL-2 Signaling," The Journal of Immunology, vol. 161:5430-5437 (1998).
Fallon, Eric M. et al., "Increased Endosomal Sorting of Ligand to Recycling Enhances Potency of an Interleukin-2 Analog," The Journal of Biological Chemistry, vol. 275(10):6790-6797 (2000).

Fehniger, Todd A. et al., "Interleukin 15: biology and relevance to human disease," Blood, vol. 97(1):14-32 (2001).
Fyfe, Gwendolyn et al., "Results of Treatment of 255 Patients With Metastatic Renal Cell Carcinoma Who Received High-Dose Recombinant Interleukin-2 Therapy," Journal of Clinical Oncology, vol. 13(3):688-696 (1995).
Guthridge, Mark A. et al., "Mechanism of Activation of the GM-CSF, IL-3, and IL-5 Family of Receptors," Stem Cells, vol. 16:301-313 (1998).
Hemar, Agnes et al., "Endocytosis of Interleukin 2 Receptors in Human T Lymphocytes: Distinct Intracellular Localization and Fate of the Receptor alpha, beta, and gamma Chains," The Journal of Cell Biology, vol. 129(1):55-64 (1995).
Hori, Toshiyuki et al., "Establishment of an Interleukin 2-Dependent Human T Cell Line From a Patient With T Cell Chronic Lymphocyte Leukemia Who Is Not Infected With Human T Cell Leukemia/Lymphoma Virus," Blood, vol. 70 (4):1069-1072 (1987).
Jacobson, Elizabeth Leef et al., "Rational interleukin 2 therapy for HIV positive individuals: Daily low doses enhance immune function without toxicity," Proc. Natl. Acad. Sci. USA, vol. 93:10405-10410 (1996).
Konrad, Michael W. et al., "Pharmacokinetics of Recombinant Interleukin 2 in Humans," Cancer Research, vol. 50:2009-2017 (1990).
Leclair, Kenneth P. et al., "The p50 subunit of NF-kappaB associates with the Nf-IL6 transcription factor," Proc. Natl. Acad. Sci. USA, vol. 89:8145-8149 (1992).
Liang, Shu-Mei et al., "Studies of Structure-Activity Relationships of Human Interleukin-2," The Journal of Biological Chemistry, vol. 261(1):334-337 (1986).
Liparoto, Stefano F. et al., "Analysis of the Role of the Interleukin-2 Receptor gamma Chain in Ligand Binding," Biochemistry, vol. 41:2543-2551 (2002).
Lowman, Henry B. et al., "Selecting High-Affinity Binding Proteins by Monovalent Phage Display," Biochemistry, vol. 30:10832-10838 (1991).
Mikayama, Toshifumi et al., "Molecular cloning and functional expression of a cDNA encoding glycosylation-inhibiting factor," Proc. Natl. Acad. Sci. USA, vol. 90:10056-10060 (1993).
Nelson, Brad H. et al., "Biology of the Interleukin-2 Receptor," Advances in Immunology, vol. 70:1-81 (1998).
Parmley, Stephen F. et al., "Antibody-selectable filamentous fd phage vectors: affinity purification of target genes," Gene, vol. 73:305-318 (1988).
Rao, Balaji M. et al., "High-Affinity CD25-Binding IL-2 Mutants Potently Stimulate Persistent T Cell Growth," Biochemistry, vol. 44:10696-10701 (2005).
Brekke, Ole Henrik et al., "Structure-function Relationships of Human IgG," The Immunologist, vol. 2(4):125-130 (1994).
Morrison, Sherie L. et al., "Structural Determinants of Human IgG Function," The Immunologist, vol. 2(4):119-124 (1994).
Wang, Zhi-Yong et al., "The Importance of Amino Acid Residues 62 and 126 to the Biological Function of Interleukin-2," Acta Biochimica et Biophysica Sinica, vol. 25(5):557-560 (1993).

\* cited by examiner

MYRMQLLSCI ALSLALVTNS APTSSSTKKT QLQLEHLLLD LQMILNGINN
|          |          |          |          |
-20        -10        1          11         21

YKNPKLTRML TFKFYMPKKA TELKHLQCLE EELKPLEEVL NLAQSKNFHL
|          |          |          |          |
31         41         51         61         71

RPRDLISNIN VIVLELKGSE TTFMCEYADE TATIVEFLNR WITFCQSIIS
|          |          |          |          |
81         91         101        111        121

TLT
|
131

Residues −20-133 correspond to SEQ ID NO:1
Residues 1-133 correspond to SEQ ID NO:2

FIG. 1

| #mutations | Isolates | 1 | 4 | 8 | 9 | 10 | 11 | 13 | 15 | 26 | 29 | 30 | 31 | 35 | 37 | 46 | 48 | 49 | 54 | 61 | 64 |
|---|---|---|---|---|---|---|---|---|---|---|---|---|---|---|---|---|---|---|---|---|---|
| C125S | | A | S | K | K | T | Q | Q | E | N | N | N | Y | K | T | M | K | K | K | E | K |
| Mutants from libraries with one round of mutation (from WT) ||||||||||||||||||||||
| M13 | 1 | 3 | | | | | | | | | | | | | | | | | | | |
| N31610_15 | 2 | 2 | | | | | | | | | | | | | | | | | | | R |
| M12 | 3 | 7 | | | | | | | | | | | | | | | | | | | |
| M9 | 3 | 4 | | | | | | | | | | | | | | | | | | | |
| M6 | 3 | 4 | | | | | | | | | | | | | | | | | | | |
| M5 | 4 | 1 | | | | | | | | | | | | | | | | | | | |
| N31610_12 | 4 | 1 | | | | | | | | | | D | | | | | | | | | |
| N31610_17 | 4 | 1 | | | | | | | | | | | | | | | | E | | | |
| N31610_20 | 4 | 1 | | | | | | | | | | S | | | | | | | | | |
| N31610_23 | 4 | 1 | | | | | | R | | | | | | | | | | | | | |
| N31610_25 | 4 | 1 | | | | | | | | | | S | | | | | | | | | |
| N31610_13 | 5 | 1 | | | | T | | | | | | | | R | | L | | R | | | |
| M16 | 6 | 1 | | | | | | | | K | | | | | | | | | | | |
| M30 | 6 | 1 | T | | | | A | R | | | | | | | | | | | | | |
| N31610_18 | 7 | 1 | | | | | | R | | K | | | | R | | | E | | | | |
| N31610_11 | 8 | 1 | | P | R | | | | | | | | | | | | | | | | |
| Mutants from libraries with two rounds of mutation ||||||||||||||||||||||
| N31610_01 | 8 | 3 | | | | | | | | | | | | | | | | | | | | |
| N31610_09 | 8 | 2 | | | | | | | | | D | S | S | C | | A | | | | | | |
| N31618_04 | 8 | 1 | | | | | | | | | D | | S | | | | | | | | | |
| N31618_08 | 9 | 5 | | | | | | | R | | | S | T | H | R | R | | E | | | | |
| N31618_14 | 10 | 1 | | | | | | | | | | S | S | H | R | A | | E | R | | | |

FIG. 2A

| | #mutations | isolates | 67 | 68 | 69 | 71 | 73 | 74 | 75 | 76 | 79 | 88 | 89 | 90 | 92 | 99 | 101 | 103 | 114 | 128 | 133 |
|---|---|---|---|---|---|---|---|---|---|---|---|---|---|---|---|---|---|---|---|---|---|
| C125S | | | E | E | V | N | A | Q | S | K | H | N | I | N | I | S | T | F | I | I | T |
| Mutants from libraries with one round of mutation (from WT) | | | | | | | | | | | | | | | | | | | | | |
| M13 | 1 | 3 | | | A | | | | | | | | | | | | | | | | |
| N31610_15 | 2 | 2 | | | A | | | | | | | | | | | | | | | | |
| M12 | 3 | 7 | | | A | | | P | | | | | | | | | | | | | |
| M9 | 3 | 4 | | | A | | | | | | | | | | | | A | | | | |
| M6 | 3 | 4 | | | A | | | P | | | | | | | | | | | | | N |
| M5 | 4 | 1 | | | A | | | P | | | | | | | | | A | | T | | |
| N31610_12 | 4 | 1 | | | A | | | P | | E | | | | | | | | | | | |
| N31610_17 | 4 | 1 | | | A | | V | P | | | | | | | | | | | | | |
| N31610_20 | 4 | 1 | | | A | | | P | | | | | | | | | | | | A | |
| N31610_23 | 4 | 1 | | | A | | | P | | | | | | | | | | S | | | |
| N31610_25 | 4 | 1 | | | A | | | P | | | | | | | | P | | | T | | |
| N31610_13 | 5 | 1 | | | A | | | P | | | | | | | | | A | S | V | | |
| M16 | 6 | 1 | | D | | | | | | | R | D | | H | | | | | | | A |
| M30 | 6 | 1 | | | A | T | | | | | | D | | | T | | | | | | |
| N31610_18 | 7 | 1 | | | A | | | P | | | R | | | H | | | | | | T | |
| N31610_11 | 8 | 1 | G | | A | | | P | | | | | | | T | | | | | | |
| Mutants from libraries with two rounds of mutation | | | | | | | | | | | | | | | | | | | | | |
| N31618_01 | 8 | 3 | | D | A | A | | P | P | | R | | | H | | | | | | T | |
| N31610_09 | 8 | 2 | | | A | | V | P | P | | R | | | | T | | | | | | |
| N31610_04 | 8 | 1 | | | A | | | P | | | | | | | | | | | | | |
| N31618_08 | 9 | 5 | | | A | | | P | | | | D | | | T | | | | | | |
| N31618_14 | 10 | 1 | | | A | R | | P | | | | D | V | | | | | | | | |

FIG. 2B

SEQUENCE LISTING

<160> NUMBER OF SEQ ID NOS: 2

<210> SEQ ID NO 1
<211> LENGTH: 153
<212> TYPE: PRT
<213> ORGANISM: Homo sapiens

<400> SEQUENCE: 1

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
```

<210> SEQ ID NO 2
<211> LENGTH: 133
<212> TYPE: PRT
<213> ORGANISM: Homo sapiens

<400> SEQUENCE: 2

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

MUTANT INTERLEUKIN-2 (IL-2) POLYPEPTIDES

CROSS REFERENCE TO RELATED APPLICATIONS

This application is a U.S. national phase application claiming the benefit of the filing date of International Application No. PCT/US2008/082528, which was filed on Nov. 5, 2008, and which claims priority to U.S. Application No. 60/985,532, filed on Nov. 5, 2007. These prior applications are hereby incorporated by reference in their entirety.

FEDERALLY SPONSORED RESEARCH OR DEVELOPMENT

This invention was made with government support under Grant Nos. AI065824 and GM08334 awarded by the National Institutes of Health. The government has certain rights in this invention.

TECHNICAL FIELD

This invention relates to mutant interleukin-2 polypeptides that act as receptor antagonists and to methods of using them to, for example, treat a patient who has cancer or a viral infection. The mutant polypeptides can also be used in various delivery systems.

BACKGROUND

Interleukin-2 (IL-2) is a cytokine that induces proliferation of antigen-activated T cells and stimulates natural killer (NK) cells. The biological activity of IL-2 is mediated through a multi-subunit IL-2 receptor complex (IL-2R) of three polypeptide subunits that span the cell membrane: p55 (IL-2Rα, the alpha subunit, also known as CD25 in humans), p75 (IL-2Rβ, the beta subunit, also known as CD122 in humans) and p64 (IL-2Rγ, the gamma subunit, also known as CD132 in humans). T cell response to IL-2 depends on a variety of factors, including: (1) the concentration of IL-2; (2) the number of IL-2R molecules on the cell surface; and (3) the number of IL-2R occupied by IL-2 (i.e., the affinity of the binding interaction between IL-2 and IL-2R (Smith, "Cell Growth Signal Transduction is Quantal" In *Receptor Activation by Antigens, Cytokines, Hormones, and Growth Factors* 766: 263-271, 1995)). The IL-2:IL-2R complex is internalized upon ligand binding and the different components undergo differential sorting. IL-2Rα is recycled to the cell surface, while IL-2 associated with the IL-2:IL-2Rβγ complex is routed to the lysosome and degraded. When administered as an intravenous (i.v.) bolus, IL-2 has a rapid systemic clearance (an initial clearance phase with a half-life of 12.9 minutes followed by a slower clearance phase with a half-life of 85 minutes) (Konrad et al., *Cancer Res.* 50:2009-2017, 1990).

SUMMARY

The present invention is based, in part, on our discovery of new IL-2 mutants. These polypeptides can be used in cancer immunotherapies and to deliver therapeutic agents to CD25-positive cells in vivo or in cell culture. Because the new mutants bind CD25 but do not activate or substantially activate the IL-2 receptor on CD25-expressing cells (e.g., T regulatory cells), we may refer to them as IL-2 antagonists. The IL-2 antagonists can be used alone in or used in combination with agents that inhibit T regulatory cells. Some of these inhibitory agents can specifically target T regulatory cells. For example, one or more of the present mutant IL-2 polypeptides can be used with one or more IL-2 agonists that specifically inhibit T regulatory cell function. Such agonists have been described by Rao et al. (*Protein Engineering* 16(12): 1081-1087, 2003) and Rao et al. (*Biochemistry* 44(31):10696-701, 2005), and in U.S. Application Publication 20050142106 (the contents of which is hereby incorporated by reference in its entirety). The agonists were engineered by directed evolution and yeast display to have high affinity binding to CD25 and increased persistence on the cell surface. In addition, they have been shown to effectively stimulate T cell growth.

The present mutant IL-2 polypeptides are IL-2 antagonists that were developed using the high CD25 binding affinity of the previously developed IL-2 agonists as a starting point. More specifically, we developed the present mutant IL-2 polypeptides (the IL-2 antagonists) by introducing additional mutations into the polypeptide sequence of the IL-2 agonist designated 2-4. Thus, the new IL-2 antagonists can differ from wild type IL-2 at one or more of the same positions at which the previously described IL-2 agonists differ from wild type IL-2, with the proviso that the amino acid sequence of the new IL-2 antagonists is not identical to any of the amino acid sequences of the IL-2 mutants described in U.S. Published Application No. 2005/0142106, which is herein incorporated by reference. For example, where the present IL-2 antagonists differ from mutant 2-4 or from the wild type IL-2 polypeptide sequence, the difference can be at position 91 and/or position 126 of SEQ ID NO:2. In one embodiment, the present IL-2 antagonists may differ from mutant 2-4 or from the wild type IL-2 polypeptide sequence at positions 91 and 126 (e.g., at positions 69, 74, 91 and 126); at positions 91 and 126 and at positions 15, 20, and 88; or at positions 91 and 126 and at positions 16, 19, 84, 123 and 129.

Generally, the result is a mutant IL-2 polypeptide that tightly binds CD25 (e.g., that binds more tightly than wild type IL-2) and sequesters CD25 from binding wild type IL-2, but does not activate the IL-2 receptor itself. A given mutant IL-2 polypeptide that does not "activate" the receptor itself when binding results in an attenuation of one or more of the events that occur downstream from IL-2 receptor activation in the same cell type upon activation by wild type IL-2. Preferably, the attenuation results in an improvement in the clinical benefit to a patient treated with the mutant IL-2 polypeptide. Thus, the present IL-2 antagonists lack or substantially lack the ability, relative to that of corresponding wild-type IL-2 (SEQ ID NO:2), to activate the IL-2 receptor. The new IL-2 antagonists can include mutations that disrupt the binding of mutant IL-2 to the IL-2 receptor β subunit (IL-2Rβ), the IL-2 receptor γ subunit (IL-2Rγ) or both the IL-2Rβ and the IL-2Rγ, relative to that of corresponding wild type IL-2 (SEQ ID NO:2).

IL-2R activation can be measured functionally, for example, by assaying markers for early events following receptor activation (e.g., phosphorylation of proteins in the JAK/STAT signaling pathway, for example, STAT 5 phosphorylation) or later stage, downstream events that follow IL-2R activation (for example, cell proliferation). Cells treated with the mutant IL-2 polypeptides of the invention can have levels of phosphorylated STAT5 that are not statistically different from those of untreated control cells or levels that are less than 1%, 2%, 5%, 10%, 15%, 20%, 25% or 50% of those in cells treated with wild type IL-2 (SEQ ID NO:2). Cells treated with the IL-2 antagonists of the invention can have proliferation rates that are not statistically different from those of untreated control cells or levels that are less than 1%, 2%, 5%, 10%, 15%, 20%, 25% or 50% of those in cells treated with wild type IL-2 (SEQ ID NO:2). The mutants may also be characterized in terms of their affinity equilibrium constant ($K_d$), for example by directly measuring binding affinity of the mutant IL-2 polypeptide to IL-2Rβ and/or IL-2Rγ.

The affinity of the mutant IL-2 polypeptides for IL-2Rα may be similar to that of wild type IL-2 or may increase by, for example, at least about 2%, 5%, 10%, 15%, 20%, 25%, 50%, or more relative to wild type IL-2 (SEQ ID NO:2); or by, for example, 2-, 5-, 10-, 15-, 20-, 25-, 50-fold or more). We may also refer to an increase in the time (or average time) the mutant IL-2 persists on a cell surface or to the rate at which it dissociates from its receptor or a subunit thereof. The mutants may also be characterized in terms of their affinity equilibrium constant ($K_d$).

While receptor binding affinities can be measured, and while there are a variety of ways to characterize the altered receptor interaction, the scope of the present invention encompasses mutant IL-2 polypeptides that have the structure described below and that confer a clinical benefit on a patient to whom they are administered that is equivalent to, or, preferably, in some way superior to, the benefit the patient would experience following treatment with wild-type IL-2 (SEQ ID NO:2). In other words, with respect to function, the present IL-2 mutants may have an decreased ability to activate IL-2 signaling via IL-2Rβ, IL-2Rγ or both relative to that of corresponding wild-type IL-2 (SEQ ID NO:2) and an increased affinity for IL-2Rα to any degree that is sufficient to improve their utility as IL-2-based therapeutic agents, regardless of the extent of the improvement or the way in which activation or affinity is changed, measured, or described. Potential advantages of the present mutants are described further below.

Accordingly, the present invention features mutant interleukin-2 (IL-2) polypeptides having an amino acid sequence that is at least 80% identical to SEQ ID NO:2 (a wild type human IL-2 polypeptide) and that: (a) binds CD25 but does not activate the IL-2 receptor (e.g., on a CD25-positive cell such as a T regulatory cell) and (b) comprises a mutation at position 91 or position 126 of SEQ ID NO:2. Thus, the mutant interleukin-2 (IL-2) polypeptides include an amino acid sequence that is at least 80% identical to SEQ ID NO:2 (e.g., 85, 87, 90, 95, 97, 98, or 99% identical) and that bind an IL-2 receptor α subunit (IL-2Rα) and that lack or substantially lack the ability, relative to wild type IL-2 (SEQ ID NO:2) to activate the IL-2 receptor. The mutant polypeptides may bind an IL-2 receptor α subunit (IL-2Rα) with an affinity that is greater than the affinity with which wild type IL-2 (SEQ ID NO:2) binds the IL-2Rα. The amino acid sequence within mutant IL-2 polypeptides can vary from SEQ ID NO:2 by virtue of containing (or only containing) one or more amino acid substitutions, which may be considered conservative or non-conservative substitutions. Non-naturally occurring amino acids can also be incorporated. Alternatively, or in addition, the amino acid sequence can vary from SEQ ID NO:2 (which may be considered the "reference" sequence) by virtue of containing and addition and/or deletion of one or more amino acid residues. The substituted amino acid can have a side chain of the same type as the residue it is replacing (e.g., a neutral, basic, or acidic side chain; or a polar or non-polar side chain).

The mutation can include the substitution, addition, or deletion of amino acids from a wild type IL-2. More specifically, the amino acid sequence can differ from that of SEQ ID NO:2 by virtue of a mutation at either position 91 or position 126. Where the mutations are substitutions, the valine at position 91 can be replaced with a charged amino acid, for example, an arginine; the glutamine at position 126 can be replaced, for example, with threonine or isoleucine. Other exemplary substitutions include replacement of the aspartic acid at position 88 with arginine; replacement of the glutamic acid at position 15 with tryptophan, arginine, lysine, asparagine or leucine; replacement of the valine at position 69 with alanine, and replacement of the glutamine at position 74 with proline. Thus, for example, the mutant IL-2 polypeptide of the invention can be an amino acid sequence that is 80% identical to SEQ ID NO:2 and that comprises a mutation at position 91. In another embodiment, the mutant IL-2 polypeptide of the invention can be an amino acid sequence that is 80% identical to SEQ ID NO:2 and that comprises a mutation at position 126.

The amino acid sequence of the mutant IL-2 polypeptides can differ from that of SEQ ID NO:2 at least one position one of the following positions of SEQ ID NO:2: 1, 4, 8, 9, 10, 11, 13, 15, 16, 19, 20, 26, 29, 30, 31, 35, 37, 46, 48, 49, 54, 61, 64, 67, 68, 69, 71, 73, 74, 75, 76, 79, 88, 89, 90, 91, 92, 99, 101, 103, 114, 125, 126, 128, or 133 (or combinations thereof) with the proviso that the amino acid sequence is not identical to any of the amino acid sequences of the IL-2 mutants described in U.S. Published Application No. 2005/0142106 (for example, the present mutant IL-2 polypeptides may have one or more additional mutations, as described herein). As noted, as few as one of these positions may be altered, as may two, three, four, five, six, seven, eight, nine, ten, or 11 or more (including up to all) of the positions. For example, the amino acid sequence can differ from SEQ ID NO:2 at positions 69 and 74 and further at one or more of positions 15, 20, 30, 35, 91, 126 and 128. The amino acid sequence can also differ from SEQ ID NO:2 at one of the following sets of positions: (a) positions 64, 69, and 74; (b) positions 69, 74, and 101; (c) positions 69, 74, and 128; (d) positions 30, 69, 74, and 103; (e) positions 49, 69, 73, and 76; (f) positions 69, 74, 101, and 133; (g) positions 30, 69, 74, and 128; (h) positions 69, 74, 88, and 99; (i) positions 30, 69, 74, and 128; (j) positions 9, 11, 35, 69, and 74; (k) positions 1, 46, 49, 61, 69, and 79; (l) positions 48, 68, 71, 90, 103, and 114; (m) positions 4, 10, 11, 69, 74, 88, and 133; (n) positions 15, 30 31, 35, 48, 69, 74, and 92; (o) positions 30, 68, 69, 71, 74, 75, 76, and 90; (p) positions 30, 31, 37, 69, 73, 74, 79, and 128; (q) positions 26, 29, 30, 54, 67, 69, 74, and 92; (r) positions 8, 13, 26, 30, 35, 37, 69, 74, and 92; (s) positions 29, 31, 35, 37, 48, 69, 71, 74, 88, and 89; (t) positions 69, 74 and 91; (u) positions 69, 74 and 126; (v) position 91; (w) position 126; (x) position 69, 74 and 15. Aside from mutations at these positions, the amino acid sequence of the mutant IL-2 polypeptide can otherwise be identical to SEQ ID NO:2. With respect to specific substitutions, the amino acid sequence can differ from SEQ ID NO:2 by virtue of having one or more of the following mutations: A1T, S4P, K8R, K9T, T10A, Q11R, Q13R, E15K, E15W, D20R, D20, K, D20, N, D20L, N26D, N29S, N30S, N30D, N30T, Y31H, Y31C, K35R, T37A, T37R, M46L, K48E, K49R, K49E, K54R, E61D, K64R, E67G, E68D, V69A, N71T, N71A, N71R, A73V, Q74P, S75P, K76E, K76R, H79R, N88D, I89V, N90H, V91R, V91K, I92T, S99P, T101A, F103S, I114V, Q126T, I128T, I128A, T133A, or T133N. Our nomenclature is consistent with that of the scientific literature, where the single letter code of the amino acid in the wild-type or reference sequence is followed by its position within the sequence and then by the single letter code of the amino acid with which it is replaced. Thus, A1T designates a substitution of the alanine residue a position 1 with threonine. Other mutant polypeptides within the scope of the invention include those that include a mutant of SEQ ID NO:2 having substitutions at V69 (e.g., A) and Q74 (e.g., P). For example, the amino acid sequence can include one of the following sets of mutations with respect to SEQ ID NO:2: (a) K64R, V69A, and Q74P; (b) V69A, Q74P, and T101A; (c) V69A, Q74P, and I128T; (d) N30D, V69A, Q74P, and F103S; (e) K49E, V69A, A73V, and K76E; (f) V69A, Q74P, T101A, and T133N; (g) N30S, V69A, Q74P, and I128A; (h) V69A, Q74P, N88D, and S99P; (i) N30S, V69A, Q74P, and I128T; (j) K9T, Q11R, K35R, V69A, and Q74P; (k) A1T, M46L, K49R, E61D, V69A, and H79R; (l) K48E, E68D, N71T, N90H, F103S, and I114V; (m) S4P, T10A, Q11R, V69A, Q74P, N88D, and T133A; (n) E15K, N30S Y31H, K35R, K48E, V69A, Q74P, and I92T; (o) N30S, E68D, V69A, N71A, Q74P, S75P, K76R, and N90H; (p) N30S, Y31C, T37A, V69A, A73V, Q74P, H79R, and I128T; (q) N26D, N29S, N30S, K54R, E67G, V69A, Q74P, and I92T; (r) K8R, Q13R, N26D, N30T, K35R, T37R, V69A, Q74P, and I92T; and (s) N29S, Y31H, K35R, T37A, K48E, V69A, N71R, Q74P, N88D, and I89V; t) V69A, Q74P, and V91R; u) V69A, Q74P, and Q126T; v) D20R, V69A, and Q74P; w) D20K, V69A, and Q74P; x) D20R, V69A, and Q74P; y) D20N, V69A, and Q74P; and z) D20L, V69A, and Q74P.

With respect to IL-2 antagonism, the mutant IL-2 polypeptides of the invention can block STAT5 phosphorylation with a Ki of about 200 pM, about 180 pM, about 160 pM, about 140 pM, about 120 pM, about 100 pM, about 80 pM, about 60 pM or less. The mutant IL-2 polypeptides of the invention can block IL-2 mediated cell growth at an EC50 of about 5 pM, 3 pM, 2 pM, 1 pM, 0.5 pM, 0.2 pM or less. With respect to affinity, the mutant IL-2 polypeptides of the invention can bind to the IL-2Rα subunit with a $K_d$ of less than about 28 nM (e.g., less than about 25 nM; less than about 5 nM; about 1 nM; less than about 500 pM; or less than about 100 pM). More specifically, a mutant IL-2 polypeptide can have an affinity equilibrium constant less than 1.0 nM (e.g., about 0.8, 0.6, 0.4, or 0.2 nM). Affinity can also be expressed as a relative rate of dissociation from an IL-2Rα or from an IL-2 receptor complex (e.g., a complex expressed on the surface of a cell or otherwise membrane bound). For example, the mutant IL-2 polypeptides can dissociate from, for example, IL-2Rα, at a decreased rate relative to a wild-type polypeptide (e.g., SEQ ID NO:2). Alternatively, affinity can be characterized as the time, or average time, a mutant IL-2 polypeptide persists on, for example, the surface of a cell expressing an IL-2R. For example, a mutant IL-2 polypeptide can persist on the receptor for at least about 2, 5, 10, 50, 100, or 250 times (or more) as long as a wild-type form of the interleukin (e.g., SEQ ID NO:2).

The IL-2 mutants can further include a heterologous amino acid sequence. For example, an IL-2 antagonist can be fused or otherwise joined at the N- or C-terminal to a heterologous amino acid sequence that increases the circulating half-life of the mutant IL-2 polypeptide, enhances expression of the mutant IL-2 polypeptide, directs cellular localization of the mutant IL-2 polypeptide, or serves as a marker or tag. Alternatively, or in addition, the heterologous amino acid sequence can be an antigen or a toxin.

One target for the present IL-2 antagonists is regulatory T cells, i.e., T cells that typically express an array of markers that includes FoxP3 and CD25, as well as CD4, GITR, CTLA-4 and folate receptor 4, which normally keep the immune system "in check" and can help prevent self-reactive immune responses and autoimmunity. In cancer, however, T regulatory cells can dampen an otherwise beneficial anti-tumor immune response. For that reason, inhibiting T regulatory cells is desirable in the context of cancer immunotherapy. IL-2 antagonists that inhibit T regulatory cells can be used alone as a therapeutic. Thus, the present methods encompass methods of treating a patient who has cancer, or who is at risk of developing cancer, by administering an IL-2 antagonist, which may be one of the mutant IL-2 polypeptides described herein. The methods can be similarly applied to a patient who has a viral infection or who is at risk of developing a viral infection.

The present IL-2 mutants can also be used in combination with cancer vaccines or in the course of adoptive T cell therapy. In that therapy, T cells are harvested from a cancer patient and activated ex vivo. Tumor-specific T cells can be selected, and the activated T cells are treated in a way that stimulates their proliferation (e.g., with a mutant IL-2 agonist). The T cells are then administered to the patient to attack and eliminate the tumor. The present IL-2 mutants can be used in the context of T cell transfer, as they can be administered to the patient who is scheduled to receive the activated T cells. Thus, the present methods encompass methods of preparing a patient for adoptive T cell transfer by administering an IL-2 antagonist. One would activate and stimulate the proliferation of T cells ex vivo (e.g., by exposing the T cells to an IL-2 agonist) and administer the T cells and an IL-2 antagonist to the patient. The IL-2 antagonist could be administered to the patient prior to administering the treated T cells, which may be autogeneic or allogeneic T cells. The patient may have a renal carcinoma, a melanoma, or be HIV-positive, and any of the present treatment methods can include a step of identifying a patient likely to benefit from the treatment.

Current treatments to deplete lymphocytes in humans include chemotherapeutic agents such as cyclophosphamide or fludarabine, but these are non-specific and can have toxic side effects (Dudley et al., *Science* 298(594):850-854, 2002). Therefore, the present, targeted approach, may be preferable in preparing patients for adoptive T cell therapy.

Another use for the present IL-2 mutants is in the CD25-targeted delivery of therapeutics. For delivery, CD25 is acting as a cell surface marker for ligand binding instead of as a molecule that alters biological activity. The present IL-2 mutants can be attached to liposomal carriers (as has been done for IL-2; see Neelapu et al., *Clin. Cancer Res.* 10:8309-8317, 2004). In other delivery systems (i.e., where delivery is not facilitated with a liposome), one can employ nanoparticles such as those described in Green et al. (*Nano Lett.* 7(4):874-879, 2007) and in U.S. Pat. Nos. 5,565,215 and 5,543,158. The IL-2 mutants can be attached to the nanoparticles in a variety of ways. For example, one could use a peptide linker (e.g., a polyglutamate linker). The mutant polypeptides may also be held by electrostatic interactions.

Regardless of the precise configuration of the delivery molecule or system, the present IL-2 mutants can be attached to, or delivered with, a polypeptide-based therapeutic such as a tumor antigen or toxin (e.g., diphtheria toxin) or with a nucleic acid that alters (e.g., inhibits) gene expression (e.g., a transcription factor or an inhibitor of a transcription factor). The nucleic acid can mediate RNAi or be a micro RNA. For example, one could deliver a Foxp3 siRNA to CD25 expressing cells. Cross reactivity would not be a concern if using Foxp3 siRNA because non-regulatory T cells that express CD25 do not express Foxp3, and would unlikely be affected by Foxp3 siRNA. However, Foxp3 has been shown to be a "master control" gene in T regulatory cells and is sufficient to express the regulatory T cell phenotype when expressed in T cells (Walker et al., *J. Clin. Invest.* 112:1437-1443, 2003). Thus, it is likely that silencing Foxp3 in T regulatory cells will abrogate its suppressive functions. Targeted delivery is a huge challenge in gene therapy, and the use of IL-2 antagonists for ligand mediated gene delivery would allow for effective inhibition of T regulatory cells in a specific manner. The use of IL-2 antagonists for nanoparticle gene delivery is desirable over wild type IL-2 or IL-2 superagonists because IL-2 antagonists are able to target CD25 and bind tightly without activating the receptor. Also, because IL-2 and its variants are relatively small molecules (~17 kDa), more IL-2 antagonists can coat the nanoparticle and provide a higher valency than larger CD25 targeting molecules such as full IgG antibodies.

Thus, the invention features delivery systems that include an IL-2 mutant polypeptide (e.g., an IL-2 mutant and a therapeutic agent or a nanoparticle, an IL-2 antagonist, and a therapeutic agent such as a tumor antigen, a toxin, or a nucleic acid). The nanoparticle can be made from one or more polymers or copolymers and may be biodegradable.

Physiologically acceptable compositions that include the mutant IL-2 polypeptides described herein are also within the scope of the present invention. A mutant IL-2 polypeptide of the invention can be supplied in a lyophilized form and reconstituted with sterile water for injection, with mannitol, sodium dodecyl sulfate (SDS), and a buffer such as monobasic and/or dibasic sodium phosphate. Antibiotics, preservatives, and other agents (such as anti-caking agents) may be included if desired.

Any of the mutant IL-2 polypeptides of the invention can be glycosylated or non-glycosylated and/or phosphorylated or non-phosphorylated.

Nucleic acid molecules that encode any of the mutant IL-2 polypeptides of the invention are also within the scope of the invention. The nucleic acids are useful, for example, in making the polypeptides of the present invention and as therapeutic agents. They may be administered to cells in culture or in vivo and may include a secretory signal that directs or facilitates secretion of the mutant IL-2 polypeptide from the cell. Also within the scope of the invention are expression vectors and host cells that contain or include nucleic acids of the invention (described further below). While we may refer to the nucleic acids as "isolated," we note that, by definition, the mutant IL-2 polypeptides of the invention are not wild-type polypeptides and, as such, would not be encoded by naturally occurring nucleic acids. Thus, while the polypeptides and nucleic acids of the present invention may be "purified," "substantially purified," or "isolated," they need not be so in order to be distinguished from naturally occurring materials.

While dosages are also discussed further below, the mutant IL-2 polypeptides of the invention are, due to their improved affinity for their receptor, expected to stimulate longer-term expansion of lymphocytes. It should, therefore, be possible to administer a smaller dosage or the same dosage less frequently than has been used with IL-2-based therapeutics to date. We further expect the mutant IL-2 polypeptides of the invention to produce less NK cell stimulation and, therefore, lessen the toxic side effects that may be associated with IL-2-based therapeutics. In addition, because the mutant polypeptides can contain a relatively small number of mutant amino acid residues, we expect they will not be immunogenic or will not induce a great immune response.

Although methods and materials similar or equivalent to those described herein can be used in the practice or testing of the present invention, suitable methods and materials are described below. Other features and advantages of the invention will be apparent from the following detailed description, and from the claims.

DESCRIPTION OF THE DRAWINGS

FIG. 1 is a representation of IL-2 from GenBank® (P01585: Interleukin-2 precursor (IL-2) (T cell growth factor) (TCGF) (Aldesleukin) [gi: 124325] (SEQ ID NO:1). The C125 residue is underlined. Residues numbered 1-133 correspond to the mature form of human IL-2 (SEQ ID NO:2).

FIGS. 2A-2B represent a Table that illustrates the positions and identity of amino acid substitutions in mutant IL-2 polypeptides with increased affinity for IL-2Rα (i.e., IL-2 agonists). FIG. 2A depicts the mutations in residues 1-64 of IL-2, and FIG. 2B depicts the mutations in residues 65-133 of IL-2. N31610__25_ is also referred to as mutant WE3. N31610__18_ is also referred to as mutant WC9. N31610__01_ is also referred to as mutant 1a-1. N31618__08_ is also referred to as mutant 1b-8. N31618__14_ is also referred to as mutant 2-4.

FIG. 3B depicts a close-up of the IL-2/IL-2Rβ interface with V91. FIG. 3C depicts a close-up of the IL-2/IL-2Rγ interface with Q126.

FIG. 5A depicts the effect of increasing concentrations of IL-2 on STAT5 phosphorylation in Kit225 cells in the absence of antagonist. FIG. 5B depicts the effect of IL-2 mutants Q126T and V91R on STAT5 phosphorylation in Kit225 cells. FIG. 5C depicts the effect IL-2 mutants Q126T and V91R on Kit225 cell proliferation. Error bars represent the standard deviation of the cell viability at each data point measured in triplicate. These data are representative of three independently repeated experiments.

FIG. 6A depicts the results of a phosphorylated STAT5 assay in Kit225 cells for the two mutants, Q126T and V91R, in the presence of 25 pM wild type IL-2. FIG. 6B depicts the results of a Kit225 cell proliferation assay for the two mutants, Q126T and V91R, in the presence of 25 pM wild type IL-2. 100 nM of Q126T or V91R was able to antagonize 25 pM wild type IL-2. FIG. 6C depicts antagonism of STAT5 phosphorylation in primary human Treg cells ex vivo in the presence of 40 pM wild type IL-2. Fluorescence was normalized to a value of 1.0 for 40 pM IL-2 in the absence of antagonist, and 0.0 in the absence of either antagonist or agonist.

DETAILED DESCRIPTION

Figure 3A:
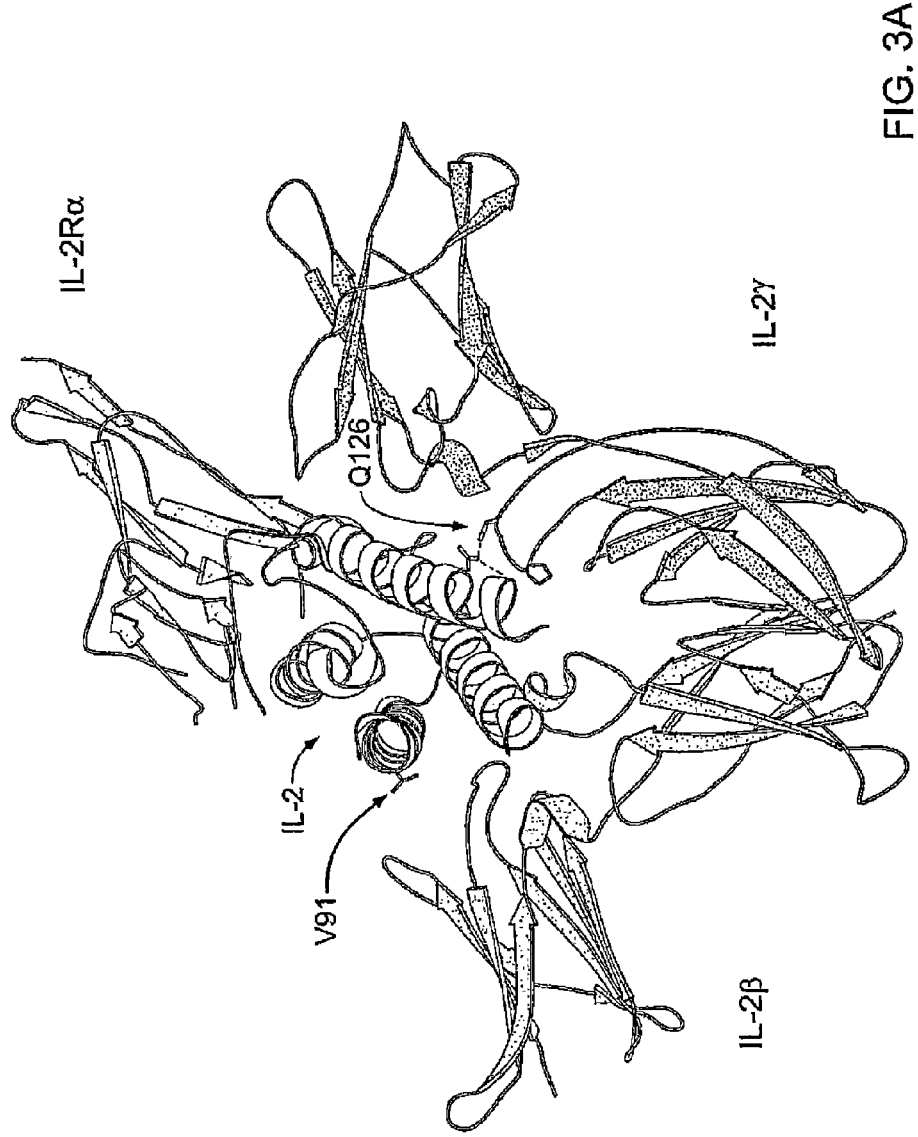
FIGS. 3A, 3B and 3C depict structural information useful in mutant IL-2 antagonist design. 3A depicts the crystal structure of IL-2 complexed with the full IL-2 receptor complex (IL-2Rα, IL-2Rβ, and IL-2Rγ), shown with the valine 91 and glutamine 126 residues highlighted.

IL-2-based therapeutics have been exploited to stimulate the proliferation of T cells in the course of treatment for metastatic renal carcinoma and melanoma (Atkins et al., *J. Clin. Oncol.* 17:2105-2116, 1999; Fyfe et al., *J. Clin. Oncol.* 13:688-96, 1995). However, a narrow therapeutic window has hampered these therapies. Undesirable inflammatory responses are activated at IL-2 concentrations above 100 pM through stimulation of NK cells (Jacobson et al., *Proc. Natl. Acad. Sci. USA* 93:10405-10, 1996; Smith, *Blood* 93:1414-23, 1993), while stimulation of T cells is not achieved below 1 pM. Given the rapid systemic clearance of IL-2 (an initial clearance phase with a half-life of 12.9 minutes followed by a slower phase with a half-life of 85 minutes (Konrad et al., *Cancer Res.* 50:2009-17, 1990)), it is difficult to maintain therapeutic concentrations of IL-2 (1-100 pM) for a sustained period.

The expression of IL-2Rα is upregulated in antigen-activated T cells (Smith, *Annu. Rev. Cell Biol.* 5:397-425, 1989; Theze et al., *Immunology Today* 17:481-486, 1996). NK cells in general express only the IL-2Rβ and IL-2Rγ subunits (Voss et al., *J. Exp. Med.* 176:531-541, 1992), so enhanced affinity for IL-2Rα would be expected to increase the specificity of IL-2 for activated T cells relative to NK cells. Manipulation of the binding affinities to these receptor subunits might be used to alter the biological response to IL-2 and potentially create an improved therapeutic. Screening of over 2,600 IL-2 variants created by combinatorial cassette mutagenesis has led to the isolation of an IL-2 variant (L18M, L19S) with increased potency (Berndt et al., *Biochemistry* 33:6571-6577, 1994; this mutant is also referred to as 2D1). 2D1 internalized by receptor-mediated endocytosis is recycled to a greater extent than wild-type IL-2, leading to decreased depletion of 2D1 in cell culture and hence improved biological potency (Fallon et al., *J. Biol. Chem.* 275:6790-6797, 2000). The 2D1 mutant is explicitly excluded from the mutant IL-2 polypeptides of the present invention (as is C125S).

Site-directed mutagenesis was also utilized to isolate IL-2 variants causing reduced stimulation of NK cells via reduced binding to IL-2Rβ and IL-2Rγ (Shanafelt et al., *Nature Biotechnol.* 18:1197-1202, 2000; this mutant is also referred to as BAY 50-4798 and is also explicitly excluded from the scope of the present invention). Increasing the affinity of IL-2 for IL-2Rα at the cell surface will increase receptor occupancy within a limited range of IL-2 concentration, as well as raise the local concentration of IL-2 at the cell surface.

Mutant IL-2 Polypeptides

The invention features mutant IL-2 polypeptides, which may be, but are not necessarily, substantially purified and which can function as antagonists of wild-type IL-2 (inhibiting one or more of the biological activities of IL-2 (e.g., stimulation of cellular proliferation)). IL-2 has been characterized as a T cell growth factor that induces proliferation of antigen-activated T cells and stimulation of NK cells.

A mutant IL-2 polypeptide includes (or, in other embodiments, is limited to) an amino acid sequence that is at least 80% identical to SEQ ID NO:2 and that binds CD25 CD25 but does not activate the IL-2 receptor on T regulatory cells. For example, a mutant IL-2 polypeptide can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-2. For example, where the mutant IL-2 polypeptide is mutant only by virtue of amino acid substitutions, up to 26 amino acid residues of SEQ ID NO:2 can be changed. For example, the amino acid residues at position 91 and/or position 126 can be changed. Additional changes may be the same as one or more of those previously described in the IL-2 agonists of U.S. Application Publication 20050142106, the content of which is hereby incorporated by reference in its entirety. In other words, the present mutant IL-2 polypeptides can have a mutation in one or more of the same positions as the mutant IL-2 polypeptide agonists described in U.S. Application Publication 20050142106 and, in addition, will have one or more mutations that were not present in the previously described mutants. For example, the mutant IL-2 polypeptides of the present invention can differ from SEQ ID NO:2 by virtue of a mutation at least one of the following positions—1, 4, 8, 9, 10, 11, 13, 15, 26, 29, 30, 31, 35, 37, 46, 48, 49, 54, 61, 64, 67, 68, 69, 71, 73, 74, 75, 76, 79, 88, 89, 90, 92, 99, 101, 103, 114, 125, 128, or 133 of SEQ ID NO:2—and will have at least one mutation at at least one other position (e.g., position 15, 20, 88, 91, or 126 of SEQ ID NO:2). For example, the mutant IL-2 polypeptides can have mutations (e.g.; single amino acid substitutions) at positions 69, 74, 91 (e.g., V91R) and 126 (e.g., Q126T). Alternatively, or in addition, the mutant IL-2 polypeptides can have mutations at positions 69, 74, 15 (e.g., E15W or E15N), 20 (e.g., D20R, D20K, D20N, or D20L), and/or 88 (e.g., D88R).

More generally, the mutant IL-2 polypeptides can include one or more mutations that increase the affinity for the alpha subunit of the IL-2 receptor, relative to wild type, and one or more mutations that decrease the affinity or disrupt binding to either the beta or gamma IL-2R subunits. For the latter, the mutant IL-2 polypeptide can include a mutation on IL-2 at the binding domain to either IL-2Rβ or IL-2Rγ (e.g., at one or more of positions 16, 19, and 84 for the beta subunit and/or at one or more of positions 123 and 129 for the gamma subunit). Accordingly, in one embodiment, the mutant IL-2 polypeptide includes (or is limited to), an amino acid sequence that is at least 80% identical to SEQ ID NO:2 and binds an IL-2R α subunit (CD25) but does not activate the IL-2 receptor. The IL-2 receptor can be one expressed by a living cell (e.g., a T regulatory cell). The mutation can be, or can include, a mutation at position 91 and/or position 126 of SEQ ID NO:2.

The term "identity," as used herein in reference to polypeptide or DNA sequences, refers to the subunit sequence identity between two molecules. When a subunit position in both of the molecules is occupied by the same monomeric subunit (i.e., the same type of amino acid residue (e.g., alanine in the same position in both of a first and a second polypeptide) or nucleotide), then the molecules are identical at that position. The similarity between two amino acid (polypeptide) or two nucleotide sequences is a direct function of the number of identical positions. In general, the sequences are aligned so that the highest order match is obtained. If necessary, identity can be calculated using published techniques and widely available computer programs, such as the GCS program package (Devereux et al., *Nucleic Acids Res.* 12:387, 1984), BLASTP, BLASTN, FASTA (Atschul et al., *J. Molecular Biol.* 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The mutant IL-2 polypeptides can be at least or about 50%, at least or about 65%, at least or about 70%, at least or about 80%, at least or about 85%, at least or about 87%, at least or about 90%, at least or about 95%, at least or about 97%, at least or about 98%, or at least or about 99% identical to wild-type IL-2 (in its precursor form or, preferably, the mature form). The mutation can consist of a change in the number or content of amino acid residues. For example, the mutant IL-2 polypeptide can have a greater or a lesser number of amino acid residues than wild-type IL-2. Alternatively, or in addition, the mutant polypeptide can contain a substitution of one or more amino acid residues that are present in the wild-type IL-2. The mutant IL-2 polypeptide can differ from wild-type IL-2 by the addition, deletion, or substitution of a single amino acid residue, for example, a substitution of the residue at position 91 of SEQ ID NO:2. Similarly, the mutant polypeptide can differ from wild-type by a substitution of two amino acid residues, for example, the residues at positions 91 and/or 126 of SEQ ID NO:2. Similarly, the mutant polypeptide can differ from wild-type by a substitution of three amino acid residues, for example, the residues at positions 91, 126, and one or more of: 1, 11, 46, 48, 49, 61, 64, 68, 69, 71, 74, 79, 90, 101, 103, 114, 128, and 133 of SEQ ID NO:2.

By way of illustration, a polypeptide that includes an amino acid sequence that is at least 95% identical to a reference amino acid sequence of SEQ ID NO:2 is a polypeptide that includes a sequence that is identical to the reference sequence except for the inclusion of up to five alterations of the reference amino acid of SEQ ID NO:2. For example, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino (N-) or carboxy (C-) terminal positions of the reference amino acid sequence or anywhere between those terminal positions, interspersed either individually among residues in the reference sequence or in one or more contiguous groups within the reference sequence.

The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine. These mutations can be at amino acid residues that contact IL-2Rα.

More specifically, a mutation (whether conservative or non-conservative, by way of addition(s) or deletion(s)) can be made at one or more of positions 1, 4, 8, 9, 10, 11, 13, 15, 26, 29, 30, 31, 35, 37, 46, 48, 49, 54, 61, 64, 67, 68, 69, 71, 73, 74, 75, 76, 79, 88, 89, 90, 91, 92, 99, 101, 103, 114, 125, 126, 128, or 133 of SEQ ID NO:2. For example, the mutation can be: A1T, S4P, K8R, K9T, T10A, Q11R, Q13R, E15K, N26D, N29S, N30S, N30D, N30T, Y31H, Y31C, K35R, T37A, T37R, M46L, K48E, K49R, K49E, K54R, E61D, K64R, E67G, E68D, V69A, N71T, N71A, N71R, A73V, Q74P, S75P, K76E, K76R, H79R, N88D, I89V, N90H, V91R, I92T, S99P, T101A, F103S, I114V, Q126T, I128T, I128A, T133A, or T133N. Additions, deletions, and substitutions of more than two residues, and substitutions at other positions may produce a similarly useful (i.e., therapeutically effective) mutant IL-2 polypeptide. As noted, any of the mutants described herein (e.g., the mutant M6, M1, C1, N31610_25_ (aka WE3), N31610_18_ (aka WC9), N31610_01_ (aka 1a-1), N31618_08_ (aka 1b-8), and N31618_14_ (aka 2-4) can optionally include a substitution of the cysteine residue at position 125 (e.g., a substitution to serine) and/or a deletion of the alanine residue at position 1 of SEQ ID NO:2. Any of the mutants described herein, including those just mentioned in which the cysteine residue at position 125 and/or the alanine residue at position 1 is altered can, more specifically, include a mutation at position 15, 16, 19, 20, 69, 74, 84, 88, 91, or 123, 126 and/or 129 of SEQ ID NO:2.

Although we favor the term "polypeptide," we may also use the terms "protein" or "peptide" to refer to any chain of amino acid residues, regardless of its length or post-translational modification (e.g., glycosylation or phosphorylation). In the event the mutant IL-2 polypeptides of the invention are "substantially pure," they can be at least 60% by weight (dry weight) the polypeptide of interest, for example, a polypeptide containing the mutant IL-2 amino acid sequence. For example, the polypeptide can be at least or about 75%, 80%, 85%, 90%, 95% or 99%, by weight, the polypeptide of interest. Purity can be measured by any appropriate standard method, for example, column chromatography, polyacrylamide gel electrophoresis, or HPLC analysis.

In general, the polypeptides used in the practice of the instant invention will be synthetic, or produced by expression of a recombinant nucleic acid molecule. In the event the polypeptide is a chimera (e.g., a fusion protein containing at least a mutant IL-2 polypeptide antagonist and a heterologous polypeptide), it can be encoded by a hybrid nucleic acid molecule containing one sequence that encodes all or part of the mutant IL-2, and a second sequence that encodes all or part of the heterologous polypeptide. For example, the mutant IL-2 polypeptide may be fused to a hexa-histidine tag to facilitate purification of bacterially expressed protein, or to a hemagglutinin tag to facilitate purification of protein expressed in eukaryotic cells.

The techniques that are required to make mutant IL-2 polypeptides are routine in the art, and can be performed without resort to undue experimentation by one of ordinary skill in the art. For example, a mutation that consists of a substitution of one or more of the amino acid residues in IL-2 can be created using a PCR-assisted mutagenesis technique (e.g., as known in the art and/or described herein for the creation of mutant IL-2 polypeptides). As one non-limiting example, the valine residue at position 91 can be changed to, for example, alanine. Mutations that consist of deletions or additions of amino acid residues to an IL-2 polypeptide can also be made with standard recombinant techniques. In the event of a deletion or addition, the nucleic acid molecule encoding IL-2 is simply digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

In addition to generating mutant polypeptides via expression of nucleic acid molecules that have been altered by recombinant molecular biological techniques, mutant polypeptides can be chemically synthesized. Chemically synthesized polypeptides are routinely generated by those of skill in the art.

As noted above, the mutant IL-2 polypeptide antagonists can also be prepared as fusion or chimeric polypeptides that include a mutant IL-2 polypeptide and a heterologous polypeptide (i.e., a polypeptide that is not IL-2 or a mutant thereof) (see, e.g., U.S. Pat. No. 6,451,308). The heterologous polypeptide can increase the circulating half-life of the chimeric polypeptide in vivo, and may, therefore, further enhance the properties of the mutant IL-2 polypeptides. The polypeptide that increases the circulating half-life may be a serum albumin, such as human serum albumin, or the Fc region of the IgG subclass of antibodies that lacks the IgG heavy chain variable region. The Fc region can include a mutation that inhibits complement fixation and Fc receptor binding, or it may be lytic, i.e., able to bind complement or to lyse cells via another mechanism, such as antibody-dependent complement lysis (ADCC; see, e.g., U.S. Pat. No. 6,410, 008).

The "Fc region" can be a naturally occurring or synthetic polypeptide that is homologous to the IgG C-terminal domain produced by digestion of IgG with papain. IgG Fc has a molecular weight of approximately 50 kDa. The mutant IL-2 polypeptides can include the entire Fc region, or a smaller portion that retains the ability to extend the circulating half-life of a chimeric polypeptide of which it is a part. In addition, full-length or fragmented Fc regions can be variants of the wild-type molecule. That is, they can contain mutations that may or may not affect the function of the polypeptides; as described further below, native activity is not necessary or desired in all cases.

The Fc region can be "lytic" or "non-lytic," but is typically non-lytic. A non-lytic Fc region typically lacks a high affinity Fc receptor binding site and a C' 1q binding site. The high affinity Fc receptor binding site of murine IgG Fc includes the Leu residue at position 235 of IgG Fc. Thus, the Fc receptor binding site can be destroyed by mutating or deleting Leu 235. For example, substitution of Glu for Leu 235 inhibits the ability of the Fc region to bind the high affinity Fc receptor. The murine C' 1q binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a lytic IgG Fc region has a high affinity Fc receptor binding site and a C'1q binding site. The high affinity Fc receptor binding site includes the Leu residue at position 235 of IgG Fc, and the C' 1q binding site includes the Glu 318, Lys 320, and Lys 322 residues of IgG1. Lytic IgG Fc has wild-type residues or conservative amino acid substitutions at these sites. Lytic IgG Fc can target cells for antibody dependent cellular cytotoxicity or complement directed cytolysis (CDC). Appropriate mutations for human IgG are also known (see, e.g., Morrison et al., *The Immunologist* 2:119-124, 1994; and Brekke et al., *The Immunologist* 2:125, 1994).

In other embodiments, the chimeric polypeptide can include the mutant IL-2 polypeptide antagonist and a polypeptide that functions as an antigenic tag, such as a FLAG sequence. FLAG sequences are recognized by biotinylated, highly specific, anti-FLAG antibodies, as described herein (see also Blanar et al., *Science* 256:1014, 1992; LeClair et al., *Proc. Natl. Acad. Sci. USA* 89:8145, 1992). In some embodiments, the chimeric polypeptide further comprises a C-terminal c-myc epitope tag.

In other embodiments, the chimeric polypeptide includes the mutant IL-2 polypeptide antagonist and a heterologous polypeptide that functions to enhance expression or direct cellular localization of the mutant IL-2 polypeptide, such as the Aga2p agglutinin subunit (see, e.g., Boder and Wittrup, *Nature Biotechnol.* 15:553-7, 1997).

Chimeric polypeptides can be constructed using no more than conventional molecular biological techniques, which are well within the ability of those of ordinary skill in the art to perform.

In other embodiments, a chimeric polypeptide including a mutant IL-2 and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135.

Nucleic Acid Molecules Encoding Mutant IL-2 Polypeptides

The mutant IL-2 polypeptide antagonist, either alone or as a part of a chimeric polypeptide, such as those described above, can be obtained by expression of a nucleic acid molecule. Thus, nucleic acid molecules encoding polypeptides containing a mutant IL-2 are considered within the scope of the invention. Just as mutant IL-2 polypeptides can be described in terms of their identity with wild-type IL-2 polypeptides, the nucleic acid molecules encoding them will necessarily have a certain identity with those that encode wild-type IL-2. For example, the nucleic acid molecule encoding a mutant IL-2 polypeptide can be at least 50%, at least 65%, preferably at least 75%, more preferably at least 85%, and most preferably at least 95% (e.g., 99%) identical to the nucleic acid encoding wild-type IL-2 (e.g., SEQ ID NO:2).

The nucleic acid molecules of the invention can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The isolated nucleic acid molecules of the invention can include fragments not found as such in the natural state. Thus, the invention encompasses recombinant molecules, such as those in which a nucleic acid sequence (for example, a sequence encoding a mutant IL-2) is incorporated into a vector (e.g., a plasmid or viral vector) or into the genome of a heterologous cell (or the genome of a homologous cell, at a position other than the natural chromosomal location).

As described above, the mutant IL-2 polypeptide of the invention may exist as a part of a chimeric polypeptide. In addition to, or in place of, the heterologous polypeptides described above, a nucleic acid molecule of the invention can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-hosphotransferase (HPH), thymidine kinase (TK), lacz (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter.

The nucleic acid molecules of the invention can be obtained by introducing a mutation into IL-2-encoding DNA obtained from any biological cell, such as the cell of a mammal. Thus, the nucleic acids of the invention (and the polypeptides they encode) can be those of a mouse, rat, guinea pig, cow, sheep, horse, pig, rabbit, monkey, baboon, dog, or cat. Typically, the nucleic acid molecules will be those of a human.

Expression of Mutant IL-2 Gene Products

The nucleic acid molecules described above can be contained within a vector that is capable of directing their expression in, for example, a cell that has been transduced with the vector. Accordingly, in addition to mutant IL-2 polypeptides, expression vectors containing a nucleic acid molecule encoding a mutant IL-2 polypeptide and cells transfected with these vectors are among the preferred embodiments.

Vectors suitable for use in the present invention include T7-based vectors for use in bacteria (see, for example, Rosenberg et al., *Gene* 56:125, 1987), the pMSXND expression vector for use in mammalian cells (Lee and Nathans, *J. Biol. Chem.* 263:3521, 1988), and baculovirus-derived vectors (for example the expression vector pBacPAK9 from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance ($neo^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), *Eukaryotic Viral Vectors*, CSH Laboratory Press, Cold Spring Harbor, N.Y.).

Prokaryotic or eukaryotic cells that contain and express a nucleic acid molecule that encodes a mutant IL-2 polypeptide are also features of the invention. A cell of the invention is a transfected cell, i.e., a cell into which a nucleic acid molecule, for example a nucleic acid molecule encoding a mutant IL-2 polypeptide, has been introduced by means of recombinant DNA techniques. The progeny of such a cell are also considered within the scope of the invention.

The precise components of the expression system are not critical. For example, a mutant IL-2 polypeptide can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (*Cloning Vectors: A Laboratory Manual*, 1985 Suppl. 1987).

The expressed polypeptides can be purified from the expression system using routine biochemical procedures, and can be used, e.g., as therapeutic agents, as described herein.

Methods of Treatment

The mutant IL-2 polypeptides, and/or nucleic acids expressing them, can be administered to a subject to treat a disorder associated with abnormal apoptosis or a differentiative process (e.g., cellular proliferative disorders or cellular differentiative disorders, such as cancer, by, for example, producing an active or passive immunity).

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. The compositions of the present invention (e.g., mutant IL-2 polypeptides and/or the nucleic acid molecules that encode them) can also be administered to a patient who has a viral infection (e.g., AIDS or an influenza). As noted above, the present polypeptides can be used to treat a patient (e.g., a patient who has cancer or a viral infection) prior to, or simultaneously with, the administration of ex vivo expanded T cells. Thus, the present peptides are useful in preparing a patient for adoptive T cell therapy.

As used herein, we may use the terms "cancer" (or "cancerous"), "hyperproliferative," and "neoplastic" to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The term's "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The mutant IL-2 polypeptides can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit. Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

Other examples of proliferative and/or differentiative disorders include skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of skin disorders include psoriasis, psoriatic arthritis, dermatitis (eczema), for example, exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis. photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The skin disorder can be dermatitis, e.g., atopic dermatitis or allergic dermatitis, or psoriasis.

Pharmaceutical Compositions and Methods of Administration

The mutant IL-2 polypeptides and nucleic acids can be incorporated into compositions, including pharmaceutical compositions. Such compositions typically include the polypeptide or nucleic acid molecule and a pharmaceutically acceptable carrier. As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics) can also be incorporated into the compositions. As the mutant IL-2 polypeptides can be used in combination, the pharmaceutical compositions can include more than one of the mutant IL-2 polypeptides described herein.

A pharmaceutical composition is formulated to be compatible with its intended route of administration. The mutant IL-2 polypeptides of the invention may be given orally, but it is more likely that they will be administered through a parenteral route. Examples of parenteral routes of administration include, for example, intravenous, intradermal, subcutaneous, transdermal (topical), transmucosal, and rectal administration. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

In the event of administration by inhalation, the mutant IL-2 polypeptides, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of the mutant IL-2 polypeptides or nucleic acids can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds (mutant IL-2 polypeptides or nucleic acids) can also be prepared in the form of suppositories (e.g., with conventional suppository bases such as cocoa butter and other glycerides) or retention enemas for rectal delivery.

The compounds (mutant IL-2 polypeptides or nucleic acids) can also be administered by transfection or infection using methods known in the art, including but not limited to the methods described in McCaffrey et al. (*Nature* 418:6893, 2002), Xia et al. (*Nature Biotechnol.* 20:1006-1010, 2002), or Putnam (*Am. J. Health Syst. Pharm.* 53:151-160, 1996, erratum at *Am. J. Health Syst. Pharm.* 53:325, 1996).

In one embodiment, the mutant IL-2 polypeptides or nucleic acids are prepared with carriers that will protect the mutant IL-2 polypeptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Dosage, toxicity and therapeutic efficacy of such mutant IL-2 polypeptides or nucleic acids compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a mutant IL-2 polypeptide (i.e., an effective dosage) depends on the polypeptide selected. For instance, single dose amounts in the range of approximately 0.001 to 0.1 mg/kg of patient body weight can be administered; in some embodiments, about 0.005, 0.01, 0.05 mg/kg may be administered. In some embodiments, 600,000 IU/kg is administered (IU can be determined by a lymphocyte proliferation bioassay and is expressed in International Units (IU) as established by the World Health Organization 1st International Standard for Interleukin-2 (human)). The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the mutant IL-2 polypeptides of the invention can include a single treatment or, can include a series of treatments. In one embodiment, the compositions are administered every 8 hours for five days, followed by a rest period of 2 to 14 days, e.g., 9 days, followed by an additional five days of administration every 8 hours.

The pharmaceutical compositions can be included in a container, pack, or dispenser together with instructions for administration.

EXAMPLES

Example 1

Materials and Methods

Preparation of IL-2 mutant proteins. Single point mutations were introduced to the 2-4 coding sequence using the Quikchange kit (Stratagene, La Jolla, Calif.) according to the manufacturer's instructions. IL-2 mutants were expressed in yeast with an N-terminal FLAG tag and a C-terminal c-myc tag as previously described. The supernatant was concentrated and buffer exchanged with PBS using a 10 kDa MWCO ultrafiltration unit (Millipore, Billerica, Mass.). The retentate was purified using an anti-FLAG M2 agarose affinity gel (Sigma-Aldrich, St. Louis, Mo.), followed by size exclusion chromatography with a Superdex 75 column (GE Healthcare, Piscataway, N.J.). Elution fractions that contained only monomeric protein were pooled and the protein concentration was determined using the Micro BCA Protein Assay kit (Pierce, Rockford, Ill.). Tissue Culture. To characterize the IL-2 mutants, the human IL-2 dependent T cell line Kit225, which constitutively expresses all three subunits of the IL-2 receptor, was used. The cells were cultured in a humidified atmosphere in 5% CO2 in RPMI 1640 supplemented with 10% heat-inactivated fetal bovine serum, 40 pM IL-2, 2 mM L-glutamine, 2 mg/mL sodium bicarbonate, 50 U/mL penicillin, 50 μg/mL streptomycin and 50 μg/mL gentamicin.

Determination of IL-2Rα binding affinities of IL-2 mutants. The equilibrium binding affinities of V91R and Q126T binding to IL-2Rα were evaluated using a modification of a previously described protocol. $8 \times 10^5$ Kit225 cells were incubated in phosphate buffered saline (PBS)+0.1% bovine serum albumin (BSA) at 37° C. for 30 minutes, with varying IL-2 mutant concentrations. At low IL-2 mutant concentrations, the total volume was increased to maintain an excess number of IL-2 mutant molecules over the number of IL-2Rα. After incubation, cells were kept on ice and stained with mouse anti-FLAG monoclonal antibody M2 (Sigma Aldrich, St. Louis, Mo.), followed by an Alexa Fluor 488 conjugated goat anti-mouse antibody (Invitrogen, Carlsbad, Calif.), to detect cell-surface bound protein. The mean single-cell fluorescence was measured, and the dissociation constant ($K_D$) and the 95% confidence interval were determined as previously described, using the following equation: $F_{obs} = cL_0/(K_D + L_0)$, where $F_{obs}$ is the background-corrected mean fluorescence, $L_0$ is the initial concentration of the protein being measured, and c is the proportionality constant. The $K_D$ of IL-2 C125S, which is equivalent to aldesleukin (Proleukin, Novartis, Basel, Switzerland) and is referred to as "wild type IL-2," was also measured as a control.

Analysis of STAT5 phosphorylation. For all STAT5 phosphorylation assays, Kit225 cells were starved of IL-2 for 36 hours. $10^6$ Kit225 cells were incubated per 1 mL culture medium at 37° C. with IL-2 mutants for 30 minutes (for agonism studies), or with IL-2 mutants and 25 pM wild type IL-2 for 15 minutes (for antagonism studies). The cells were fixed and permeabilized using the method optimized by Krutzik et al. (Krutzik PO, Nolan GP. Intracellular phosphoprotein staining techniques for flow cytometry: monitoring single cell signaling events. *Cytometry A.* 2003; 55:61-70) The cells were stained with anti-pSTAT5 antibody clone 47 conjugated with Alexa Fluor 488 (BD Biosciences, San Jose, Calif.) and the mean single-cell fluorescence was measured. For antagonism studies, the half-maximal inhibitory concentration ($IC_{50}$) and the 95% confidence interval were determined using the following equation $F_{obs} = c/(1 - L_0/(IC_{50} + L_0))$, where all variables are defined above. A global fit nonlinear regression was performed for each protein, using a global $IC_{50}$ value and the proportionality constant from each of two separate experiments.

Phosphorylation-state analysis was performed on human whole blood using BD Phosflow technology according to the manufacturer's instructions (BD Biosciences, San Jose, Calif.), and as described in Maier et al. (*Proc Natl Acad Sci USA.* 104:18607-12, 2007). All human blood samples were obtained with informed consent and according to the Institutional Ethics Review Board Protocols. All blood samples were collected in sterile 10 ml lithium heparin Monoject tubes. Four milliliter of fresh, ex vivo blood from healthy control donors were used per condition and time-point. Blood samples were incubated with IL-2 in the form of aldesleukin (Proleukin, Novartis, Basel, Switzerland) or with a cocktail of IL-2 and IL-2 antagonists in 50 ml polypropylene Falcon conical tubes for 30 minutes in a 37° C. water bath. Fixation of cells and preservation of phosphorylation status was obtained by adding pre-warmed BD Lyse/Fix buffer and incubation in a 37° C. water bath. Permeabilization of cells was performed by incubation of cells in BD Perm Buffer III on ice for 30 minutes. Cells were subsequently washed twice with 2% FBS/PBS and stained using BD Staining Buffer (all reagents from BD Bioscience, San Jose, Calif.). Cells were stained using APC mouse anti-human CD4 (clone RPA-T4) (BD Bioscience, San Jose, Calif.), PE anti-human Foxp3 (clone 206D) (Biolegend, US) and Alexa Fluor-488 mouse anti-human pSTAT5 (pY694; clone 47) (BD Bioscience, San Jose, Calif.).

Kit225 Cell Proliferation Assays. Kit225 cells were starved of IL-2 for 36 hours. Then, $4 \times 10^5$ cells were incubated in 3 mL culture medium at 37° C. with IL-2 mutants, either in the absence (for agonism studies), or presence (for antagonism studies) of 25 pM wild type IL-2. At each time point, the cell viability in 100 ΞL culture medium was determined in triplicate using the CellTiter-Glo assay (Promega, Madison, Wis.) and a Cary Eclipse luminometer (Varian, Palo Alto, Calif.) according to the manufacturer's instructions.

Example 2

Design of IL-2 Mutant Antagonists

IL-2 analogue antagonists were designed using the following criteria: 1) high binding affinity to IL-2Rα, the IL-2 specific capture subunit, and 2) low predicted binding affinity to IL-2Rβ or IL-2Rγ, the two subunits responsible for receptor signaling. The high binding affinity to IL-2Rα leads to preferential IL-2Rα binding of the IL-2 analogue over wild type IL-2, while the low binding affinity to IL-2Rβ or IL-2Rγ would prevent the IL-2 analogue from activating the IL-2 receptor signal itself. We achieved the first design criterion by an engineered mutant of human IL-2 (termed "2-4") as a starting point for our IL-2 analogue. 2-4 IL-2 is an IL-2 analogue having high binding affinity to IL-2Rα. The $K_D$ of 2-4 binding to IL-2Rα is ~200 pM whereas the $K_D$ of wild type IL-2 binding to IL-2Rα is ~30 nM. 2-4 persists on the surface of cells expressing IL-2Rα for days, significantly longer than the cell surface persistence of wild type IL-2. For the second design criterion, we used the crystal structures of wild type IL-2 bound to the three IL-2 receptor subunits, to identify candidate residues likely to make energetically important interactions with the IL-2Rβ or IL-2Rγ subunits. Accordingly, we disrupted binding of 2-4 to IL-2Rβ or IL-2Rγ by introducing amino acid substitutions' predicted to disrupt the wild type binding interactions.

Recently published crystal structures of the IL-2/IL-2 receptor quaternary complex were used to determine key IL-2 residues that would make important contacts with the IL-2Rβ and IL-2Rγ subunits (Wang et al., *Science* 310:1159-1163, 2005; Stauber et al., *Proc. Natl. Acad. Sci. USA* 103:2788-2793, 2006). Five mutants, each with a single point mutation on the 2-4 background were generated in small scale pilot studies (Table I).

TABLE 1

| Mutations for Disrupting IL-2 Receptor Subunit Binding | |
|---|---|
| Subunit Binding Disrupted | Mutation |
| IL-2Rβ | D88R*, V91R |
| IL-2Rγ | Q126T, Q126I |
| IL-2Rβ and IL-2Rγ | E15W |

*Wild type IL-2 has an asparagine at position 88, but 2-4 IL-2 has a N88D substitution Several of these point mutations have been reported in the literature on a wild type IL-2 background to disrupt biological activity (Cassell et al., *Curr. Pharm. Des.* 8:2171-2183, 2002) or more explicitly, to disrupt IL-2 receptor subunit binding affinity (Shanafelt et al., *Nat. Biotechnol.* 18:1197-1202, 2000; Collins et al., *Proc. Natl. Acad. Sci. USA* 85:7709-7713, 1988; Eckenberg et al., *Cytokine* 9:488-498, 1997; and Buchli and Ciardelli, *Arch. Biochem. Biophys.* 307:411-415, 1993.

Of the five mutants generated, V91R and Q126T, which contain single residue substitutions at the binding interfaces with IL-2Rβ and IL-2Rγ, respectively, were secreted in yeast most efficiently and were characterized further (FIG. 3). On wild type IL-2, V91 is in the center of the IL-2/IL-2Rβ interface and makes van der Waals interactions with IL-2Rβ (Stauber et al., *Proc. Natl. Acad. Sci. USA* 103:2788-2793, 2006). Therefore, a charged amino acid substitution, such as arginine, at V91 was hypothesized to disrupt binding to IL-2Rβ. As for IL-2Rγ binding, previous reports have shown the importance of Q126 for biological activity (Buchli and Ciardelli, *Arch. Biochem. Biophys.* 307:411-15, 1993; Liang et al., *J. Biol. Chem.* 261:334-337, 1986).

The crystal structures used also identified Q126 as the most important IL-2 residue that interacts with IL-2Rγ (Wang et al., *Science* 310:1159-1163, 2005; Stauber et al., *Proc. Natl. Acad. Sci. USA* 103:2788-2793, 2006). Cassell and coworkers performed an extensive study of the activity of wild type IL-2 mutants on T cells with each of the 20 amino acids in the 126 position, and showed that threonine yielded the lowest activity. We assumed that this was due to abrogated IL-2Rγ binding and was the basis for introducing a Q126T mutation on the 2-4 background.

Figure 3C:
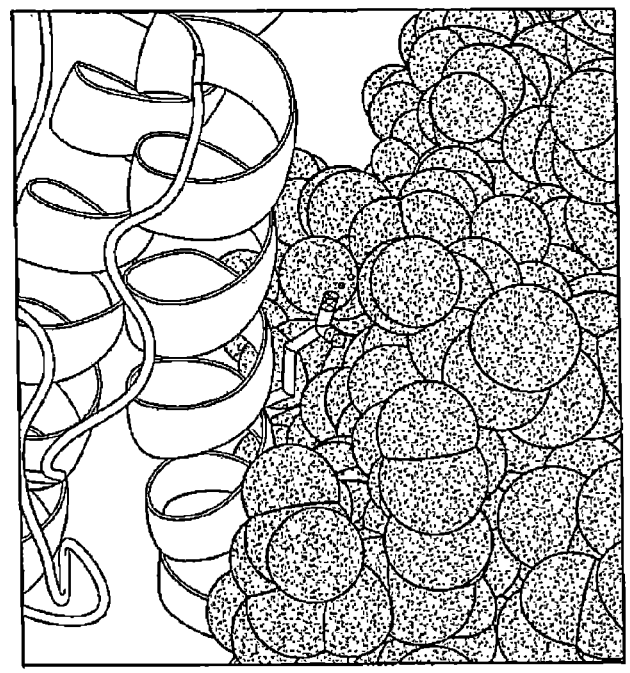
Figure 3B:
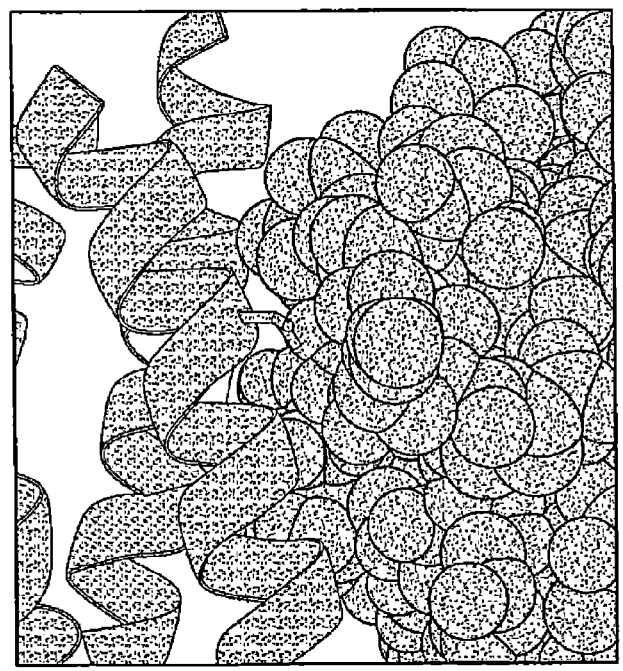

FIG. 3A shows the crystal structure of IL-2 complexed with the full IL-2 receptor complex, IL-2Rα, IL-2Rβ, and IL-2Rγ, with the valine 91 and glutamine 126 residues highlighted. Close-ups are shown of the IL-2/IL-2Rβ interface with V91 in FIG. 3B, and the IL-2/IL-2Rγ interface with Q126 in FIG. 3C.

Example 3

IL-2Rα Binding Affinity of the Mutant IL-2 Polypeptides

The first design criterion for the IL-2 antagonists was to maintain high binding affinity to IL-2Rα in order for IL-2Rα to preferentially bind the antagonist over wild type IL-2. The IL-2Rα binding affinity of the IL-2 mutants was measured in using Kit225 cells, a human T cell line that is dependent on IL-2 for growth. Kit225 constitutively expresses all three subunits of the IL-2 receptor, with IL-2Rα in ~10 fold excess. The IL-2Rα binding affinity was measured using cell surface titrations on Kit225.

Figure 4:
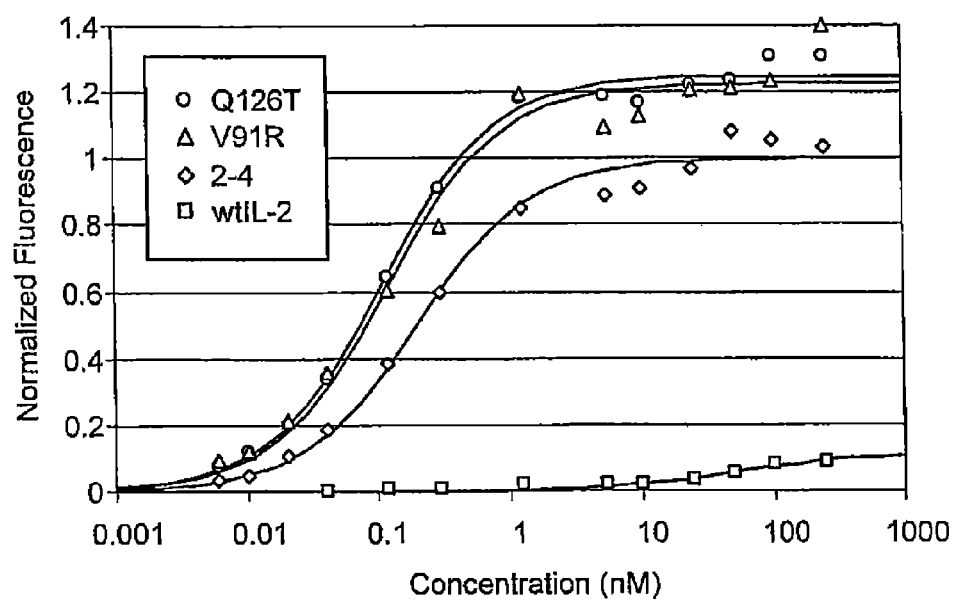
FIG. 4 is a graph depicting Kit225 cell surface titrations to measure IL-2Rα binding affinity. The binding isotherms are shown for: Q126T ($K_d$=109±19 pM), V91R ($K_d$=119±45 pM), ($K_d$=199±56 pM), and wild type IL-2 ($K_d$=46±36 nM). Fluorescence was normalized to the maximum fluorescence of 2-4 as determined by least squares regression, and $K_D$ values are reported with 95% confidence intervals.

The binding domains to each of the three IL-2 receptor subunits are on distinct areas of the surface of IL-2. Therefore, single residue substitutions at the IL-2Rβ or IL-2Rγ interfaces on the 2-4 background were estimated to have little or no effect on the binding affinity to IL-2Rα. The measured IL-2Rα binding affinities of V91R and Q126T were similar to that of 2-4, indicating that the introduction of each of the two point mutations did not disrupt high affinity binding to IL-2Rα. FIG. 4 shows the binding isotherms for: Q126T ($K_d$=109±19 pM), V91R ($K_d$=119±45 pM), 2-4 ($K_d$=199±56 pM), and wild type IL-2 ($K_d$=46±36 nM). Fluorescence was normalized to the maximum fluorescence of 2-4 as determined by least squares regression, and $K_D$ values were reported with 95% confidence intervals. In contrast, a Q126T/V91R double mutant unexpectedly had significantly lower IL-2Rα binding affinity ($K_D$=2 nM) than that of 2-4.

Example 4

Disruption of Agonism in the Mutant IL-2 Polypeptides

The second design criterion for the IL-2 antagonists was the disruption of binding affinity to the IL-2Rβ and IL-2Rγ subunits, so that the IL-2 mutants themselves would not agonize the IL-2 receptor. The binding affinities of wild type IL-2 to IL-2Rβ or to IL-2Rγ alone are relatively low, with $K_D$ values of approximately 0.5 mM and 0.7 mM, respectively. Because the affinities of the IL-2 analogues with disrupted binding interactions to IL-2Rβ or IL-2Rγ were likely be too low to be measured directly, we evaluated the effect of the IL-2 analogues on two cell-based markers for IL-2 activation.

Figure 5A:
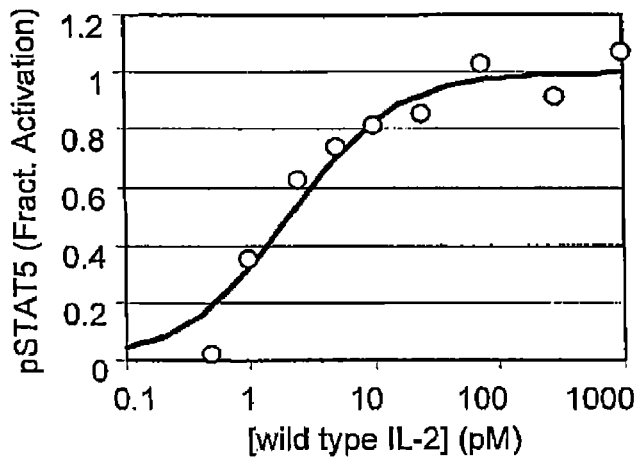
FIGS. 5A, 5B and 5C are graphs from studies illustrating the lack of agonism by Q126T and V91R.
Figure 5B:
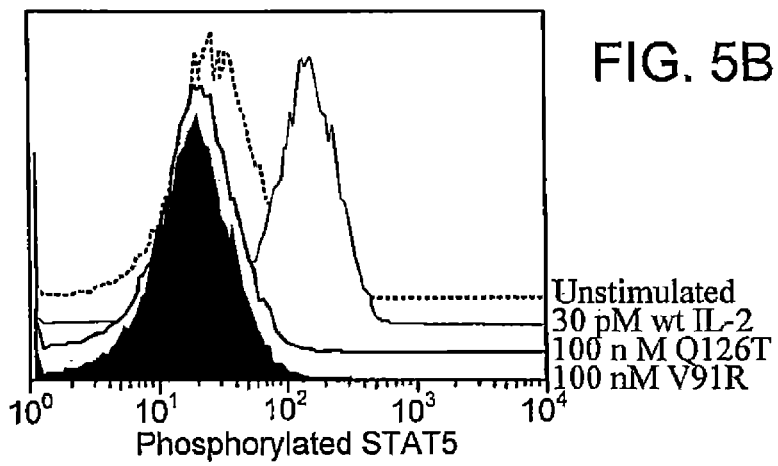

The Jak/STAT pathway is activated by the IL-2 receptor in both non-regulatory T cells and regulatory T cells. We assayed phosphorylation of STAT5 (pSTAT5) as a marker for early signaling events in IL-2 receptor activation. STAT5 phosphorylation was assayed according to the method in Example 1. STAT5 phosphorylation in Kit225 was found to be extremely sensitive to wild type IL-2, with a measured half-maximal effective concentration ($EC_{50}$) of approximately 2 pM wild type IL-2. As shown in FIG. 5A, in the absence of antagonist, the measured EC50 is 2.1±1.2 pM; these data are representative of two independently repeated experiments. However, the pSTAT5 profiles of cells treated with 100 nM V91R or Q126T were indistinguishable from those of untreated cells (FIG. 5B), indicating that the V91R and Q126T mutations severely inhibited the ability of IL-2 to activate the IL-2 receptor.

Figure 5C:
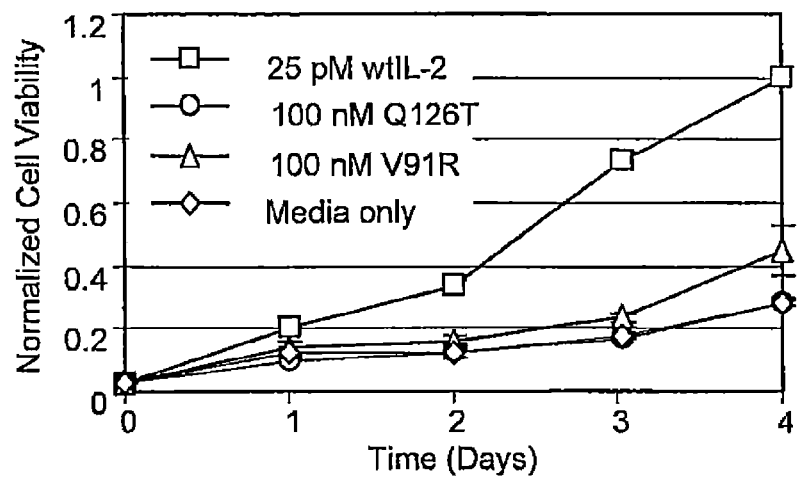

IL-2 induced cell proliferation in the IL-2 dependent Kit225 cell line was used as a marker for late signaling events in IL-2 receptor activation. Kit225 cell proliferation was analyzed according to the method in Example 1. The half-maximal effective concentration for wild type IL-2 induced cell growth was about 10 pM. In contrast, both the V91R and Q126T mutant IL-2's had minimal effects on cell growth even at concentrations as high as 100 nM (FIG. 5C). After four days of treatment, the V91R mutant treated cells showed a small increase in proliferation relative to the untreated control cells, but the effect was significantly less than the growth induced by 25 pM IL-2. Error bars in FIG. 5C represent the standard deviation of the cell viability at each data point measured in triplicate. These data were representative of three independently repeated experiments.

Example 5

Figure 6A:
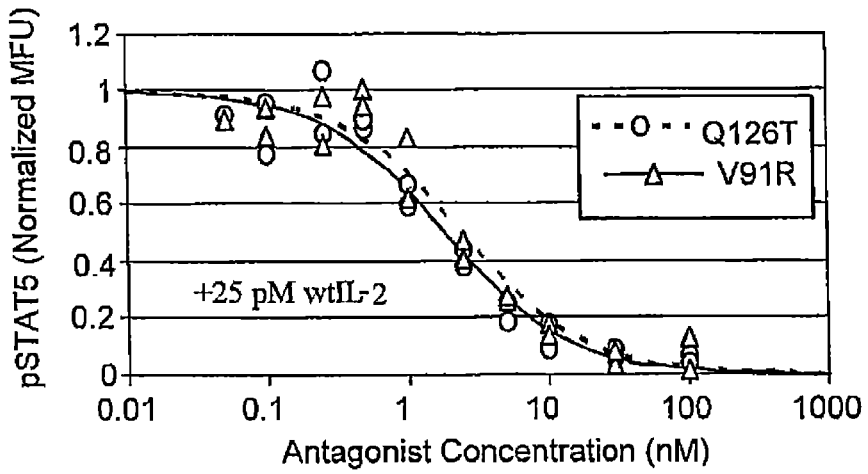
FIGS. 6A, 6B and 6C are graphs from studies of antagonism by Q126T and V91R.

Antagonism by Mutant IL-2 Polypeptides in Kit225 Cells and Primary Human Treg Cells The ability of the IL-2 mutants to antagonize the IL-2 receptor was analyzed using pSTAT5 assays as a marker for early signaling events and IL-2 induced cell proliferation as a marker for late signaling events according to the method in Example 4. The two mutants, Q126T and V91R, were assayed for antagonism in the presence of 25 pM wild type IL-2 in a phosphorylated STAT5 assay. Data for each antagonist were combined from two independent experiments. Fluorescence was normalized to the maximum fluorescence of each antagonist as determined by least squares regression. As shown in FIG. 6A, both mutants showed a dose-dependent ability to, decrease the level of IL-2 mediated pSTAT5 in Kit225 cells. The IC50 values and 95% confidence intervals for IL-2 receptor antagonism in the presence of 25 pM wild type IL-2 were 1.9±0.4 nM for Q126T, and 2.4±0.6 nM for V91R.

Figure 6B:
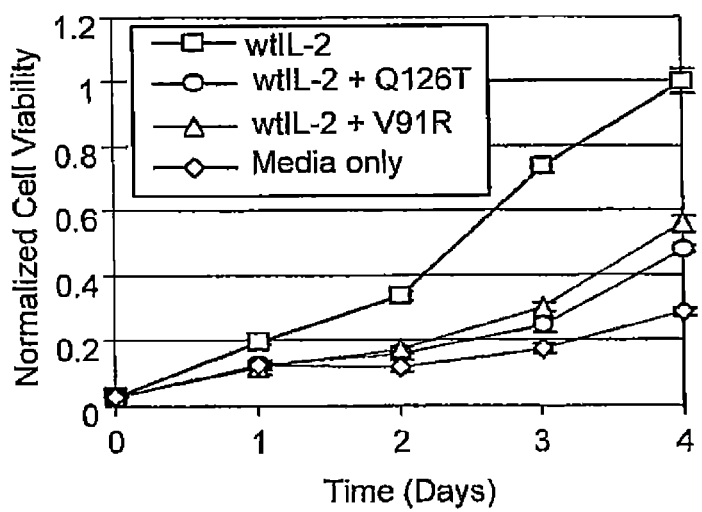

In Kit225 cell proliferation assays, V91R and Q126T effectively antagonized IL-2 receptor. As shown in FIG. 6B, 100 nM Q126T or V91R inhibited IL-2 mediated cell proliferation; the concentration of wild-type IL-2 in these experiments was 25 pM. These data were representative of three independently repeated experiments. Cell viability was normalized to the mean viability of the 25 pM wild type IL-2 group on day 4. Error bars represent the standard deviation of the cell viability at each data point measured in triplicate.

Figure 6C:
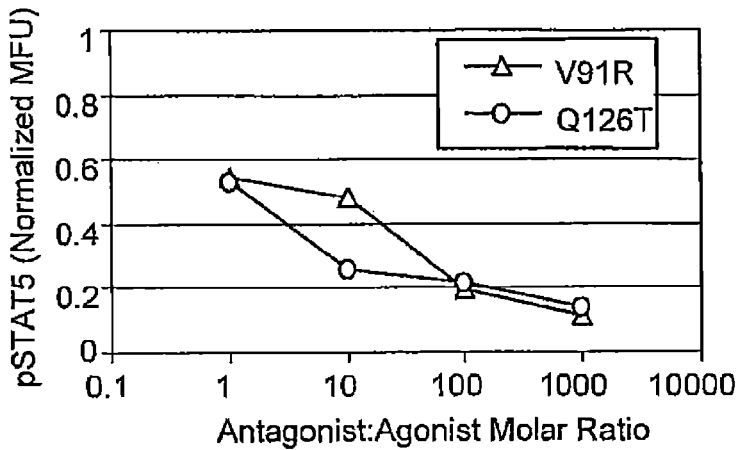
Figure 7:
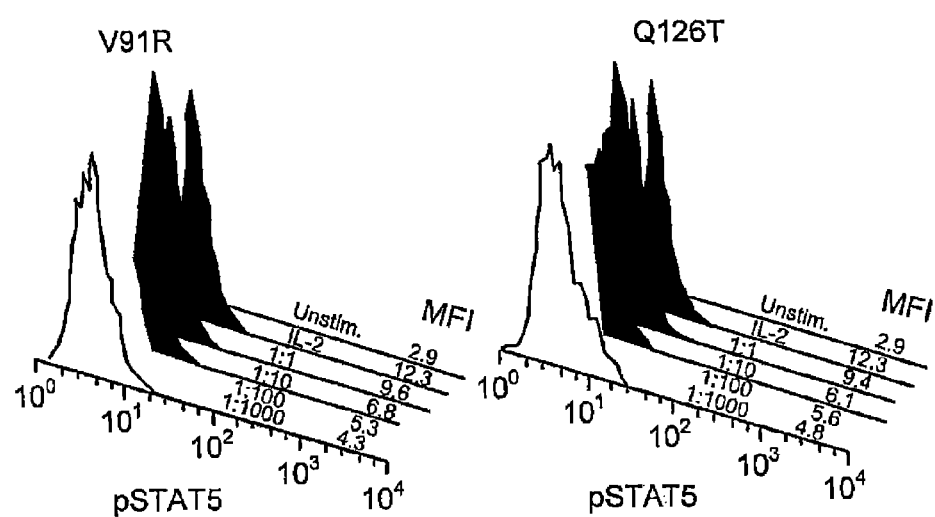
FIG. 7 depicts antagonist dose-response analysis for primary human Treg cells treated with Q126T and V91R in the presence of 40 pM wild-type IL-2.

The ability of the IL-2 analogues to antagonize STAT5 phosphorylation in primary human Treg cells ex vivo in the presence of 40 pM wild type IL-2 was measured according to the method in Example 1. Primary human Treg cells were identified based on expression of CD4 and FoxP3. Fluorescence was normalized to a value of 1.0 for 40 pM IL-2 in the absence of antagonist, and 0.0 in the absence of either antagonist or agonist. Normalized data are shown in FIG. 6C. The raw data, i.e., the flow histograms for each antagonist treatment series used to generate the curves in FIG. 6C are shown in FIG. 7. The ratios in FIG. 7 are molar ratios of wild-type IL-2 to antagonist; the data are representative of three independent experiments. Both mutants showed a dose-dependent ability to decrease the level of IL-2 mediated pSTAT5 in primary human Treg cells. The data shown in FIG. 6C and FIG. 7 indicated that these antagonists interfere with wild-type IL-2 signaling with an $IC_{50}$ similar to that measured with the Kit225 cell line.

By the Cheng-Prusoff relationship for a competitive antagonist ($IC_{50}=K_I(1+[A]/EC_{50})$, where [A]=wild type IL-2 agonist concentration), the $IC_{50}$ values measured in the Kit225 pSTAT5 assays corresponded to inhibition constant ($K_I$) values of 180 pM for V91R and 140 pM for Q126T and 95% confidence intervals of 91-270 pM and 110-330 pM, respectively, as determined by bootstrapping. These values were consistent with the direct binding affinity measured in FIG. 4. Although nanomolar concentrations of Q126T and V91R were required to antagonize 25 pM wild type IL-2, the Cheng-Prusoff relationship indicated that this is due to the high sensitivity of the Kit225 pSTAT5 assay to IL-2. The concentration of wild type IL-2 agonist, 25 pM, was over 10 times the $EC_{50}$ of the assay (FIG. 5A), indicating that the assay was being performed under highly saturating wild type IL-2 levels. Because $IC_{50}$ values were dependent on assay conditions, the measured $IC_{50}$ values of ~2 nM did not indicate the in vivo concentration required for Treg inhibition, and thus could not be used to judge accurately the effectiveness of the antagonists. Instead, a better indicator of the antagonists' effectiveness and potency was the assay-independent $K_I$ which were sub-nanomolar for both antagonists and indicate relatively potent antagonists. A similar $IC_{50}$ value was measured in the pSTAT5 assays in primary Tregs. However, a similar analysis based on the Cheng-Prusoff equation for a consistency check could not be performed, due to a lack of an $EC_{50}$ value for the assay. The donor variability in IL-2 sensitivity as well as limitations in the amount of blood taken from a single donor made it difficult to measure both an IL-2 agonist dose response (for $EC_{50}$ determination) and antagonist inhibition curves (for $IC_{50}$ determination) for use in calculating $K_I$ values in primary Tregs.

What is claimed is:

1. A mutant interleukin-2 (IL-2) polypeptide comprising an amino acid sequence set forth in SEQ ID NO:2 and further comprising an amino acid substitution at position 91 and/or position 126 of SEQ ID NO: 2, wherein the polypeptide binds CD25 but does not activate the IL-2 receptor on T regulatory cells.

2. The mutant IL-2 polypeptide of claim 1, further comprising a mutation at position 69 or position 74 of SEQ ID NO:2.

3. The mutant IL-2 polypeptide of claim 1, further comprising a heterologous amino acid sequence.

4. The mutant IL-2 polypeptide of claim 3, wherein the heterologous amino acid sequence increases the circulating half-life of the mutant IL-2 polypeptide, enhances expression of the mutant IL-2 polypeptide, directs cellular localization of the mutant IL-2polypeptide, or serves as a marker or tag.

5. A composition comprising the mutant IL-2 polypeptide of claim 1 and a physiologically acceptable carrier.

6. The mutant IL-2 polypeptide of claim 1, wherein amino acid residue 91 has been substituted.

7. The mutant IL-2 polypeptide of claim 1, wherein amino acid residue 126 has been substituted.

8. The mutant IL-2 polypeptide of claim 1, wherein amino acid residues 91 and 126 have been substituted.

9. The mutant IL-2 polypeptide of claim 1, wherein arginine is substituted for valine at position 91 and threonine is substituted for glutamine at position 126.

10. The mutant IL-2 polypeptide of claim 1, wherein arginine is substituted for valine at position 91 and isoleucine is substituted for glutamine at position 126.

11. The mutant IL-2 polypeptide of claim 1, wherein the mutant polypeptide binds to the IL-2Rα subunit with a $K_d$ of less than 28 nM.

12. The mutant IL-2 polypeptide of claim 10, wherein the mutant polypeptide binds to the IL-2Rα subunit with a $K_d$ of less than 25 nM.

13. The mutant IL-2 polypeptide of claim 11, wherein the mutant polypeptide binds to the IL-2Rα subunit with a $K_d$ of less than 5 nM.

14. The mutant IL-2 polypeptide of claim 12, wherein the mutant polypeptide binds to the IL-2Rα subunit with a $K_d$ of less than 1 nM.

15. The mutant IL-2 polypeptide of claim 12, wherein the mutant polypeptide binds to the IL-2Rα subunit with a $K_d$ of less than 500 pM.

16. The mutant IL-2 polypeptide of claim 6, wherein arginine is substituted for valine at position 91.

17. The mutant IL-2 polypeptide of claim 7, wherein threonine is substituted for glutamine at position 126.

18. The mutant IL-2 polypeptide of claim 7, wherein isoleucine is substituted for glutamine at position 126.

19. The mutant IL-2 polypeptide of claim 3, wherein the heterologous amino acid sequence increases the circulating half-life of the mutant IL-2 polypeptide, enhances expression of the mutant IL-2 polypeptide, directs cellular localization of the mutant IL-2polypeptide, or serves as a marker or tag.

20. The mutant IL-2 polypeptide of claim 3, wherein the heterologous amino acid sequence is an Fc region of an immunoglobulin, a FLAG epitope, a c-myc epitope, albumin, or an Aga2p agglutinin polypeptide.

21. The mutant IL-2 polypeptide of claim 3, wherein the heterologous amino acid sequence is the sequence of an antibody or antigen-binding fragment thereof.

22. The mutant IL-2 polypeptide of claim 3, wherein the heterologous amino acid sequence is a toxin.

23. A composition comprising the mutant IL-2 polypeptide of claim 9 and a physiologically acceptable carrier.

24. A composition comprising the mutant IL-2 polypeptide of claim 10 and a physiologically acceptable carrier.

25. A composition comprising the mutant IL-2 polypeptide of claim 16 and a physiologically acceptable carrier.

26. A composition comprising the mutant IL-2 polypeptide of claim 17 and a physiologically acceptable carrier.

27. A composition comprising the mutant IL-2 polypeptide of claim 18 and a physiologically acceptable carrier.

\* \* \* \* \*